United States Patent
Gellman et al.

(10) Patent No.: US 10,213,572 B2
(45) Date of Patent: Feb. 26, 2019

(54) NITROGEN DIOXIDE STORAGE CASSETTE

(71) Applicant: VERO BIOTECH LLC, Atlanta, GA (US)

(72) Inventors: Barry N. Gellman, Melbourne, FL (US); Eddie Tajudeen, Orlando, FL (US); Lucas Gamero, Oviedo, FL (US); Joshua Hopkins, Orlando, FL (US); Edward E. A. Bromberg, Orlando, FL (US); Ryan Denton, Cocoa, FL (US); Bryan J. Johnson, Orlando, FL (US); David Fine, Cocoa, FL (US)

(73) Assignee: VERO BIOTECH LLC, Atlanta, GA (US)

( * ) Notice: Subject to any disclaimer, the term of this patent is extended or adjusted under 35 U.S.C. 154(b) by 115 days.

(21) Appl. No.: 14/918,511

(22) Filed: Oct. 20, 2015

(65) Prior Publication Data

US 2016/0106946 A1    Apr. 21, 2016

Related U.S. Application Data

(60) Provisional application No. 62/066,345, filed on Oct. 20, 2014.

(51) Int. Cl.
| | |
|---|---|
| *A61M 16/12* | (2006.01) |
| *C01B 21/24* | (2006.01) |
| *A61M 16/00* | (2006.01) |
| *A61M 16/10* | (2006.01) |

(52) U.S. Cl.
CPC ............. *A61M 16/12* (2013.01); *C01B 21/24* (2013.01); *A61M 16/107* (2014.02); *A61M 2016/003* (2013.01); *A61M 2016/0027* (2013.01); *A61M 2202/0275* (2013.01); *A61M 2205/12* (2013.01)

(58) Field of Classification Search
CPC .............................. A61M 16/12; C01B 21/24
USPC ........................................................ 422/119
See application file for complete search history.

(56) References Cited

U.S. PATENT DOCUMENTS

| | | | |
|---|---|---|---|
| 5,827,420 A | 10/1998 | Shirazi et al. | |
| 2005/0000981 A1 | 1/2005 | Peng et al. | |
| 2008/0317874 A1 | 12/2008 | Fine et al. | |
| 2010/0043789 A1* | 2/2010 | Fine ..................... | A61M 16/00 128/203.12 |
| 2011/0168174 A1* | 7/2011 | Fine ...................... | A61K 33/00 128/202.26 |
| 2011/0240020 A1 | 10/2011 | Fine et al. | |

(Continued)

OTHER PUBLICATIONS

International Search Report dated Jan. 19, 2016, issued in International Application No. PCT/US2015/056531.

(Continued)

*Primary Examiner* — Kevin Joyner
(74) *Attorney, Agent, or Firm* — Steptoe & Johnson LLP

(57) ABSTRACT

A nitric oxide delivery system can include a cassette which is a single use disposable component used to store liquid $N_2O_4$, activate upon operator demand, convert $N_2O_4$ to $NO_2$ via a heating element(s) controlled by a console to deliver $NO_2$ at a controlled flow rate, direct concentrated $NO_2$ to a contained pair of conversion cartridges and exhaust NO gas to the console for delivery to the patient.

16 Claims, 24 Drawing Sheets

(56) References Cited

U.S. PATENT DOCUMENTS

2011/0259325 A1 10/2011 Fine et al.

OTHER PUBLICATIONS

Written Opinion of The International Searching Authority dated Jan. 19, 2016, issued in International Application No. PCT/US2015/056531.
Notification Concerning Transmittal of International Preliminary Report on Patentability (Chapter I of The Patent Cooperation Treaty) dated May 4, 2017, issued in International Application No. PCT/US2015/056531.

* cited by examiner

US 10,213,572 B2

NITROGEN DIOXIDE STORAGE CASSETTE

CLAIM FOR PRIORITY

This application claims priority under 35 U.S.C. § 119(e) to U.S. patent application Ser. No. 62/066,345 filed on Oct. 20, 2014, which is hereby incorporated by reference in its entirety.

TECHNICAL FIELD

The invention relates to systems and methods for the storage and delivery of a gas including at least 1% nitric oxide.

BACKGROUND

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia.

Generally, nitric oxide can be inhaled or otherwise delivered to the individual's lungs. Providing a therapeutic dose of NO could treat a patient suffering from a disorder or physiological condition that can be mediated by inhalation of NO or supplement or minimize the need for traditional treatments in such disorders or physiological conditions. Typically, the NO gas can be supplied in a bottled gaseous form diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, the part per million levels of $NO_2$ gas can be highly toxic if inhaled and can form nitric and nitrous acid in the lungs.

SUMMARY

In general, a cassette for conversion of nitrogen dioxide to nitric oxide can include a sealed housing, a first cartridge capable of converting nitrogen dioxide gas to nitric oxide within the sealed housing, the first cartridge comprising an inlet, a diverter, a body, an outlet, and a porous solid matrix including a reducing agent, the porous solid matrix being positioned within the first cartridge such that there is a space between the body of the first cartridge and the porous solid matrix, wherein the porous solid matrix includes an open passage parallel to the length of the body of the first cartridge, a second cartridge capable of converting nitrogen dioxide gas to nitric oxide, wherein an outlet of the first cartridge and an inlet of the second cartridge is connected, the second cartridge comprising an inlet, a diverter, a body, an outlet, and a porous solid matrix including a reducing agent, the porous solid matrix being positioned within the first cartridge such that there is a space between the body of the first cartridge and the porous solid matrix, wherein the porous solid matrix includes an open passage parallel to the length of the body of the first cartridge; and an inerting chamber including an inerting material.

In certain embodiments, the space has a width, which is a distance between the surface of the porous solid matrix to the receptacle, and the width of the space is variable along the length of the receptacle, and wherein the inlet is configured to receive a gas flow, the diverter directs the gas flow to the space between the body and the porous solid matrix, and the gas flow is fluidly communicated to the outlet through the porous solid matrix to convert nitrogen dioxide in the gas flow into nitric oxide.

In other embodiments, the width of the space decreases along a portion of the length of the receptacle.

In other embodiments, the width of the space increases along a portion of the length of the receptacle.

In other embodiments, the width of the space increases along a portion of the length of the receptacle extending from the inlet to approximately the midpoint of the receptacle, and the width of the space decreases along a portion of the length of the receptacle extending from the approximately the midpoint of the receptacle to the outlet.

In other embodiments, the sealed housing further comprises a storage device of $N_2O_4$ and $NO_2$.

In other embodiments, the storage device is contained within a shuttle tube, wherein the tube stabilizes the storage device.

In other embodiments, the shuttle tube is positioned such that the inerting chamber opens to the storage device during shipment.

In other embodiments, the inerting material undergoes a permanent color change when the storage device is broken.

In other embodiments, the sealed housing further comprises a restrictor.

In other embodiments, the restrictor connects the storage device and the first cartridge.

In other embodiments, the sealed housing further comprises a heater.

In other embodiments, the heater wraps around the storage device and controls an output of nitrogen dioxide gas by changing the temperature of the storage device.

In other embodiments, the cassette is disposable after single use.

In other embodiments, the cassette is further connected to a console, wherein the console controls the heater.

In general, a storage device of liquid nitrogen dioxide can include a vessel including an ampoule, an ampoule including liquid nitrogen dioxide, wherein the liquid nitrogen dioxide converts to nitric oxide when the ampoule is broken, a restrictor, wherein a proximal end of the restrictor is facing the ampoule and a distal end of the restrictor provides an exit for nitric oxide gas; a leak valve connected to the ampoule; and a shuttle tube containing the ampoule.

In certain embodiments, the shuttle tube connects with the restrictor when a user breaks the ampoule.

In other embodiments, the storage device is further connected to a heater.

In other embodiments, the heater is activated when a user breaks the ampoule.

In other embodiments, the storage device is further connected to an inert chamber through the leak valve.

In other embodiments, the shuttle rotates to connect the ampoule either to the inert chamber or to the restrictor.

In other embodiments, the storage devices is further connected to a mixing T-fitting.

In other embodiments, an air flows into the mixing T-fitting.

In other embodiments, the volume of the storage device is not greater than 0.53 mL.

In other embodiments, the storage is device is contained in a sealed housing.

In other embodiments, the sealed housing further includes a first cartridge capable of converting nitrogen dioxide gas to nitric oxide within the sealed housing, the first cartridge comprising an inlet, a diverter, a body, an outlet, and a porous solid matrix including a reducing agent, the porous solid matrix being positioned within the first cartridge such that there is a space between the body of the first cartridge and the porous solid matrix, wherein the porous solid matrix includes an open passage parallel to the length of the body of the first cartridge, a second cartridge capable of converting nitrogen dioxide gas to nitric oxide, wherein an outlet of the first cartridge and an inlet of the second cartridge is connected, the second cartridge comprising an inlet, a diverter, a body, an outlet, and a porous solid matrix including a reducing agent, the porous solid matrix being positioned within the second cartridge such that there is a space between the body of the second cartridge and the porous solid matrix, wherein the porous solid matrix includes an open passage parallel to the length of the body of the second cartridge; and an inerting chamber including an inerting material.

In other embodiments, the space has a width, which is a distance between the surface of the porous solid matrix to the receptacle, and the width of the space is variable along the length of the receptacle, and wherein the inlet is configured to receive a gas flow, the diverter directs the gas flow to the space between the body and the porous solid matrix, and the gas flow is fluidly communicated to the outlet through the porous solid matrix to convert nitrogen dioxide in the gas flow into nitric oxide.

In other embodiments, the width of the space decreases along a portion of the length of the receptacle.

In other embodiments, the width of the space increases along a portion of the length of the receptacle.

In other embodiments, the width of the space increases along a portion of the length of the receptacle extending from the inlet to approximately the midpoint of the receptacle, and the width of the space decreases along a portion of the length of the receptacle extending from the approximately the midpoint of the receptacle to the outlet.

Other aspects, embodiments, and features can be apparent from the following description, the drawings, and the claims.

DETAILED DESCRIPTION

When delivering nitric oxide (NO) for therapeutic use to a mammal, it can be important to avoid delivery of nitrogen dioxide ($NO_2$) to the mammal. Nitrogen dioxide ($NO_2$) can be formed by the oxidation of nitric oxide (NO) with oxygen ($O_2$). The rate of formation of nitrogen dioxide ($NO_2$) can be proportional to the oxygen ($O_2$) concentration multiplied by the square of the nitric oxide (NO) concentration. A NO delivery system can convert nitrogen dioxide ($NO_2$) to nitric oxide (NO). Additionally, nitric oxide can form nitrogen dioxide at increased concentrations.

Figure 1:
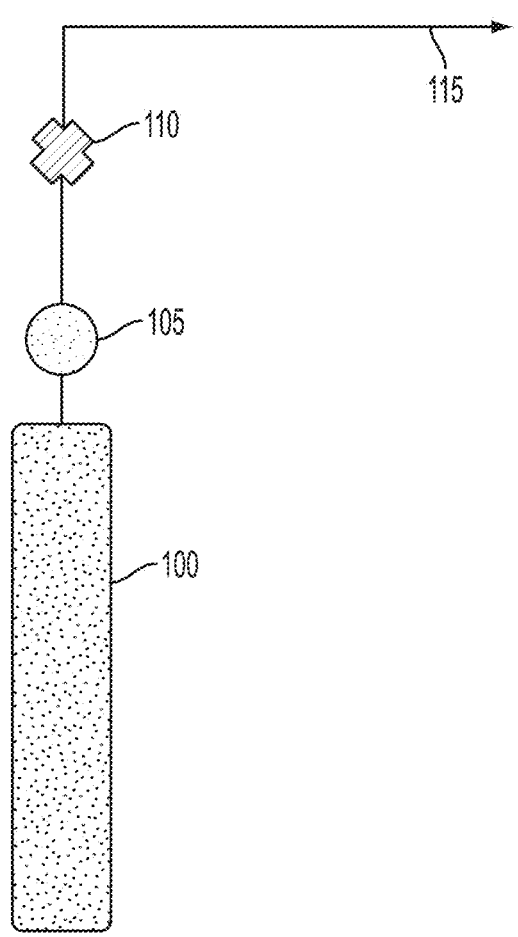
FIG. 1 is a drawing depicting a conventional nitric oxide delivery platform.

Referring to FIG. 1, platforms for delivering nitric oxide currently exist. For example, the standard platform in use can include a gas bottle 100 which contains 800 ppm NO in nitrogen ($N_2$) (FIG. 1). The nitric oxide/nitrogen gas can be released from the gas bottle 100 and the pressure and rate of the gas can be controlled using a gas regulator 105 and/or a valve 110. Using a gas bottle platform, the NO output 115 can be defined by the nitrogen dioxide concentration in the gas bottle 100 and cannot be varied by the user. For example, if the gas bottle contained 80 ppm of $NO_2$ in air or oxygen, then the output can be 80 ppm of $NO_2$ in air or oxygen. The gas can be supplied, typically, at a pressure of 2000 psi or greater. Typically, a gas bottle includes at least 99.9% $N_2$. A gas bottle platform can work well, but can be large, heavy and cumbersome because the platform can include a heavy aluminum or steel gas pressure cylinder, a gas regulator and a flow controller.

Examples of commercially available platforms are manufactured by Ikaria, two of which are the INOvent and the INOmax DS. Both of these systems use gas bottles of NO diluted in nitrogen ($N_2$), which is then mixed with oxygen enriched air to provide the inhaled NO gas. Both of these systems are designed to work with a ventilator in an intensive care setting in a hospital. These platforms are not suitable for ambulatory or home use.

Figure 2:
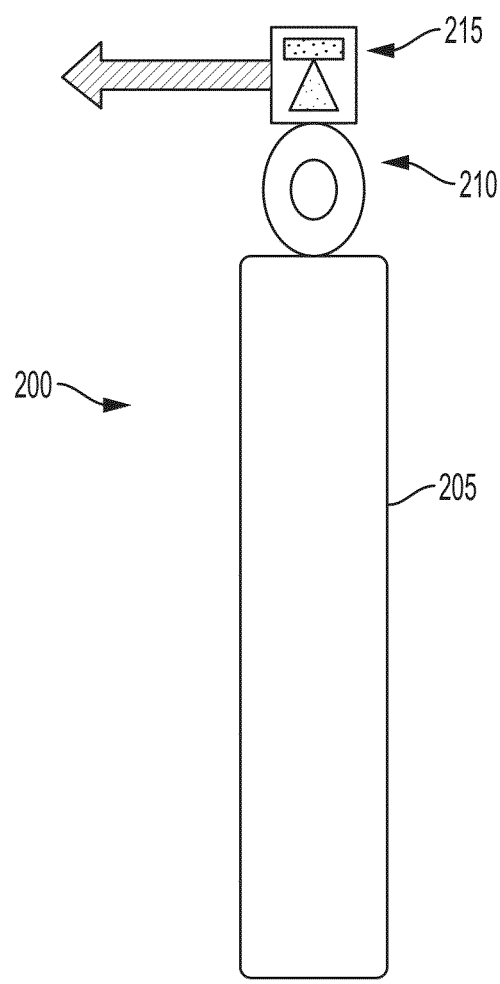
FIG. 2 is a drawing depicting a nitric oxide delivery platform.

Referring to FIG. 2, as another example, a platform can be a standalone gas bottle platform. A gas bottle platform 200 can include a gas bottle 205, a gas regulator 210 and a GeNO cartridge 215. The output from the gas cylinder can be delivered to a GeNO cartridge, where one of the oxygen atoms in the $NO_2$ is stripped out by a reducing agent, for example, ascorbic acid, to generate ultra pure NO. The GeNO cartridge is described in greater detail below and in U.S. patent application Ser. Nos. 12/500,929, 12/541,144, 12/619,959 and 12/951,811, and U.S. Pat. No. 7,560,076, each of which is incorporated by reference in its entirety. This platform has been cleared by FDA for use in two clinical trials with human patients.

Another variation for delivering NO can be to start with a $NO_2$ gas concentration of up to 2,000 ppm in air or oxygen and dilute it down to 80 ppm of $NO_2$. This set up can be even more complex in that it can require precision mass flow controllers and meters in order to get a stable mixing ratio.

As mentioned above, the disadvantage of the gas bottle platform can be that the platform can be large and heavy. The platform can also be inconvenient to use for chronic treatment as an ambulatory platform. Gas bottles can also be cumbersome when used in a confined space such as in an Intensive Care Unit, in a hospital or in a home. In addition, the gas bottles need to be tied down to prevent them from falling over and causing physical injury. Also, the regulator can break off in a fall, and the sudden venting of gas through the opening can cause the heavy bottle to become a projectile, which can penetrate numerous walls and cause injury or death. Therefore, there is a need for a nitric oxide delivery platform, which can includes a nitric oxide source which is small and portable for use in an ambulatory or home setting.

A cassette can be a fully integrated single use disposable component which can store liquid $N_2O_4$, activate (break glass ampoule) upon operator demand, convert $N_2O_4$ to $NO_2$ via a heating element(s) controlled by a console to deliver $NO_2$ at a controlled flow rate, direct concentrated $NO_2$ to a contained pair of conversion cartridges and exhaust NO gas to the console for delivery to the patient.

Figure 3A:
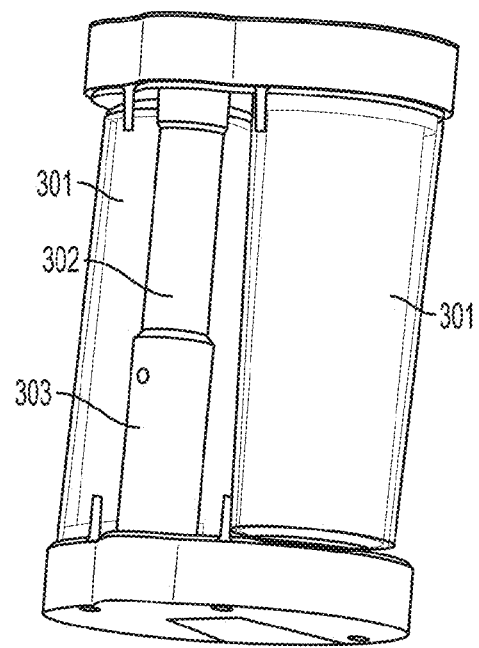
FIGS. 3A-3D are schematic drawings depicting the supply subassembly.
Figure 3B:
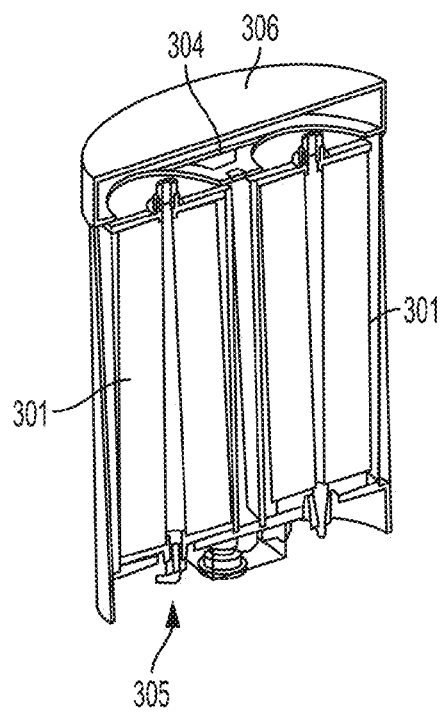
Figure 3C:
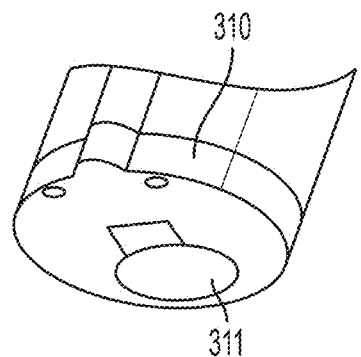
Figure 3D:
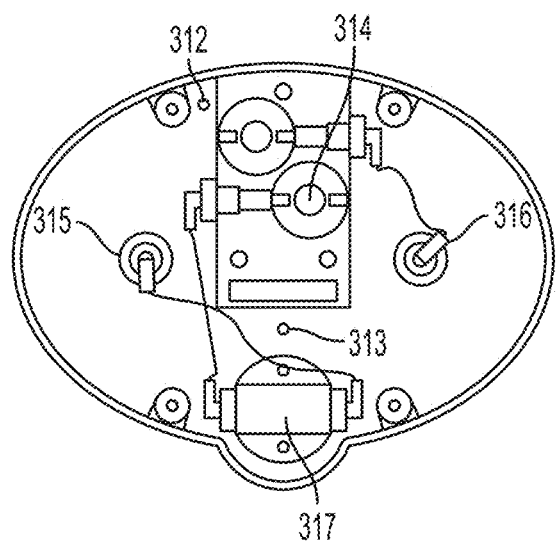

Referring to FIGS. 3A to 3D, FIG. 3A is a schematic of a cassette which includes two primary cartridges 301, a liquid module 302 containing the $N_2O_4$ ampule and shuttle mechanism, and a restrictor column assembly 303. In FIG. 3B, an inerting chamber 304 connects two primary cartridges. A cover 306 is clear to be able to see the color change of a neutralized material. Heater and thermistor contacts 305 are at the opposite end of the cover. FIG. 3C shows the cassette base 310 with access ports. The access ports are covers with a foil seal before usage. FIG. 3D shows the layout of the cassette base including a purge inlet 312, a purge outlet 313, an air inlet 314, a first primary cartridge inlet 315, a second primary cartridge inlet 316, and a restrictor "T" 317.

Cassette Integrated Safety Features

A cassette can provide safety elements to restrict and convert NO and $NO_2$ gas from discharge into the atmosphere. A liquid module can provide adequate safety features to limit $NO_2$ exposure to the equipment user or shipping carrier.

A cassette can contain the following protections for shippers and users from exposure to $NO_2$ gas exposure:

Glass Ampule—SAFETY #1

$N_2O_4$ can be contained in the liquid form and housed in a glass vial. The maximum volume $N_2O_4$ contained within the glass ampule can be 0.53 ml which is below the EPA limit should a catastrophic failure occur (inadvertent human exposure—established for catastrophic failure of an $NO_2$ gas cylinder). Environmental exposure of liquid $N_2O_4$ can diffuse into a room at a slow rate as the gas much heat up to convert into $NO_2$ as compared to a broken $NO_2$ gas regulator with contents under high pressure and immediate discharge into the room. The glass ampule can be secured to the shuttle with a Teflon shrink tube. This shrink tube can offer a number of benefits: a) stabilize the glass ampule during shipping and dampen vibration; b) provide a glass shard containment barrier.

Shuttle Seals—SAFETY #2 A&B and #3 A&B

A glass ampule can be contained within a two position component that enables glass breakage and shuttles a seal to either end (output or inerting) of the liquid vessel—each end containing a different function. A dual leak-tight safety seal is fastened to both ends of the Shuttle. The inerting seal can control gas flow to the inerting chamber of the liquid module. The output seal controls gas flow to the patient. The Shuttle is manually positioned to direct gas flow to the inerting or the output side. The seals are designed to provide redundancy by combining both a radial seal and a luer seal mating to a polished exhaust port.

Inerting Chamber—SAFETY #4

The shuttle mechanism can be positioned with the inerting chamber open to the liquid vessel during product shipment. Should the glass ampule break in transit, the entire contents of the liquid vessel can be directed to the neutralizing material to make the $NO_2$ gas inactive through chemical reaction. This provides an additional safety means to the cassette. In addition, the inerting material can undergo a permanent color change, visible through the cassette window, to provide the user with an indication that the cassette is no longer functional and should not be utilized.

Slow Leak Valve—SAFETY #5

The product can be shipped with the inerting seal in the OPEN position such that there is direct communication between the liquid chamber and the inerting material. Should the glass vial break in transit, the $NO_2$ gas can be directed to the inerting material to be neutralized. The gas flow rate into the inerting chamber can be controlled such to manage reaction temperature build-up and provide adequate time for the inerting reaction to occur.

The slow leak valve can provide an additional safety feature of reducing the rate of $NO_2$ gas discharge to the environment should a catastrophic failure occur.

Schrader-Type Valves (FIG. 4)—SAFETY #6 A&B

At the base of the cassette can be three access ports (as well as DC powered heater connectors): a room air pump inflow, a NO gas outflow, a purge inflow. All high concentration $NO_2$ gas plumbing is contained within the cassette, reducing the environmental exposure from a leak.

Figure 4:
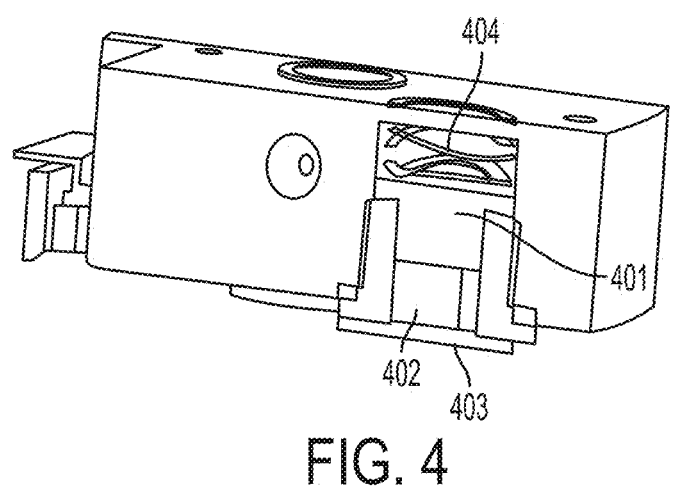
FIG. 4 is a schematic depicting a Schrader-type valve.

Referring to FIG. 4, both the air inflow and NO gas outflow ports can provide redundant seals independent from the liquid vessel shuttle mechanism in case of an outlet seal failure. These seals can be activated after insertion of the cassette into the console and upon system activation to insert the air pump inlet and NO gas outlet probes into the cassette. The Schrader-type seals are normally closed spring loaded and are mechanically displaced upon introduction of the probes from the console. Upon removal of the probes from the cassette, the schrader seals are automatically returned to the sealing positions. FIG. 4 shows schrader valve 401, console access 402, a foil seal 403, and spring(s) 404.

Tamper-Proof Seals—SAFETY #7 & #8

The base of the cassette can contain a foil seal covering the room air pump inflow and NO gas outflow ports. This seal can be punctured upon system activation (probe insertion into the cassette) and provide a tamper evident seal from the user inadvertently challenging the Schrader Seals.

The top of the cassette can contain a foil or paper seal to cover the cassette activation rotation knob. This rotation knob engages the console for activation of the glass vial breakage.

Purge Material—SAFETY #9

The cassette can contain a purge material which is used to scrub NO gas emerging from the console during system priming to eliminate air from the console lines and cassette components. This purge can be directed to the cassette purge material.

Cassette Construction—Safety #10

The liquid module can be hermetically welded aluminum and capable of withstanding internal pressures to 100 psi. All liquid module seals can be compatible with $N_2O_4$ or high concentration $NO_2$ gas and withstand temperatures to 70° C.

Cassette Packaging—Safety #11

The cassette can be initially packaged in a foil pouch as a safety and moisture barrier. Stability testing can be conducted to determine the long term need for this pouch.

Cassette Sub-Assemblies and Features

The cassette can be designed such the sub-assemblies are not positional orientation sensitive so as not to restrict cassette positioning within the console or provide transportability limitations.

Liquid Module Sub Assembly

A liquid module is a self-contained subassembly that houses the $N_2O_4$ liquid and associated integrated safeties and controls associated with the $NO_2$ gas delivery. The liquid module is initially configured such to maintain communication between the liquid vessel and the inerting chamber should a glass vial failure occur and $N_2O_4/NO_2$ fill the liquid vessel.

A liquid vessel can interface the cassette distribution manifold in a gas-tight assembly. The concentrated $NO_2$ gas flow emanating from the output of the liquid vessel and restrictor flow column can discharge into the room air pump inflow and be carried to the first primary cartridge.

The liquid module can be positioned in the cassette and on the distribution manifold such to align the activation cam in its initial position to receive the console activation knob.

A liquid vessel can be wrapped with DC electrical flexible heaters positioned about the liquid vessel and the restrictor column segment. A temperature console can control the temperature of the liquid/gas such to generate the programmed milligrams/deciliter (mg/dl) delivered to the patient line.

Cartridge Sub-Assembly

A primary cartridge can provide the means to convert $NO_2$ to NO gas through a reaction with ascorbic acid pretreated on the surfaces of the high density polyethylene and silica gel composite matrix. The cartridge should be capable of converting the contents of one liquid vial of $N_2O_4$ to NO gas. The cassette can contain two primary cartridges. The primary cartridges can come from two separate lots of production to provide a redundant $NO_2$ conversion should a "bad" of cartridges occur. The primary cartridges can be hermetically bridged in series with a conduit to couple the first primary cartridge gas outlet to the second primary cartridge gas inlet.

Cassette Distribution Manifold Sub-Assembly

The base of a cassette can contain a cassette distribution manifold. This manifold interfaces the liquid module restrictor column, the first primary cartridge gas inlet, the second primary cartridge gas outlet and the console room air pump inflow and NO gas outflow ports. In addition, a port is provided for the console to access the purge chamber.

The cassette distribution manifold can provide a gas-tight seal between the first primary cartridge gas inlet as well as the second primary cartridge gas outlet. The cassette distribution manifold can contain two schrader-like valves independent from the valves contained within the liquid module. These valves provide $NO_2$ gas escapement should the cassette be removed from the console or failure occurs to the output shuttle seal. One schrader-like seal can be incorporated into the room air pump inflow port and one schrader-like seal is incorporated into NO gas outflow port. Both valves are spring loaded normally closed and opened with the console probes. The cassette distribution manifold can interface the console with probes that contain double (serviceable) O-ring seals. These seals should be compatible with high concentration NO gas.

The base of the cassette can contain three ports as well DC electrical connectors. A foil seal can be placed over the room air pump inflow port, the NO gas outflow port and the system purge port. The foil seal(s) are intended to be punctured by the console probes (not pealed-off) and must not interfere with the O-ring seals of the probe interface.

Cassette/Console Interface

The cassette can be accessed through a cannula-like probe with double O-ring seals at each connection for redundancy in order to insure that there cannot be a leak at the connection: (1) the first connection can be for the air pump input accessed through a schrader-like safety valve; (2) the second connection can be for the output of the second primary cartridge, again through a schrader-like safety valve for control and distribution of the NO gas through the console for injection to the nasal cannula or the ventilator line.

The cassette can be accessed through a cannula-like probe with double O-ring seals at the purge port for access to the purge material from the console. The cassette can be accessed from the console for 12 or 24 VDC electrical connections to manage the flexible heaters used to control the $NO_2$ gas flow by the console control system. The connection ports must be $NO_2$ and air leak-tight to the internals of the console.

Purge Chamber

The purge chamber can contain a scrubbing material to the console system plumbing exhaust. The potassium permanganate with sodium permanganate with activated charcoal can be utilized. The purge chamber may be vented to the atmosphere after the NO gas is neutralized by the medium or be directed to a pressure relief valve. The scrubbing material used during the start-up and purge process to scrub any NOx before exhaust to the environment.

Cassette Housing and Assembly

The cassette housing can contain the above sub-assemblies into a single container. The assembly should be non-user accessible. This may include a welded assembly or a "special key" to open the cassette at the manufacturing site. Appropriate labeling as authorized by the regulatory bodies must be included on the cassette and associated packaging. The top of the cassette can contain a tamper resistant strip to isolate the activation cam from the user to inhibit manual activation of the liquid module during cassette handling.

Cartridge

Figure 5B:
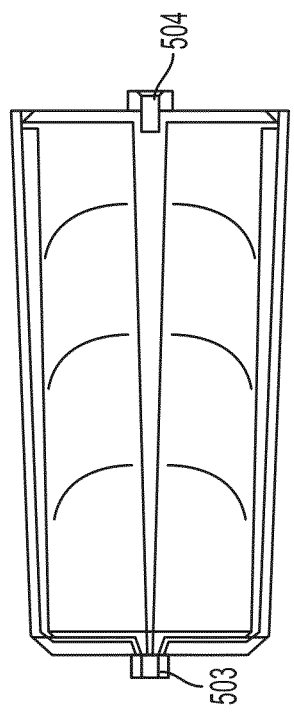
FIG. 5B is a cross-section of FIG. 5A.
Figure 5A:
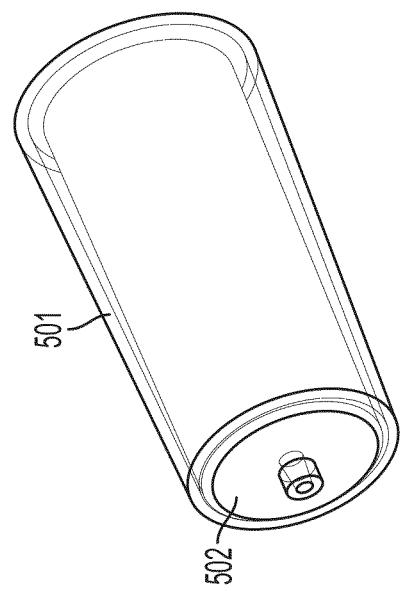
FIG. 5A is a schematic depicting a cartridge.

A cartridge is a system used to convert $NO_2$ gas generated from the liquid module to inhaled NO gas delivered to the patient and controlled by the console. The cartridge is housed in the cassette that interfaces the console. To minimize risk two such cartridges, each sized to be able to convert one complete $N_2O_4$ charge, and each from a different manufacture lot are included in the cassette. Referring to FIG. 5A, FIG. 5A is a gross view of a cartridge with a cartridge housing 501 and a composite cap 502 secured to inlet end of the composite. Referring to FIG. 5B, FIG. 5B depicts a cross-section of FIG. 5A with a cap 503 secured to an inlet having an end 504.

A composite is utilized to provide a porous rigid matrix consisting of a blend of silica gel and high density polyethylene (HDPE). The HDPE is the binding material utilized to construct the rigid matrix. A sintering process is utilized to secure the structure. The composite can be designed to have as high a percentage (can be between 40% and 85%) of silica gel as possible and still maintain mechanical integrity. To achieve a composite that is uniform, the HDPE particle size distribution can be chosen to be similar to that of the silica gel. To achieve this, the HDPE particles are sieved using a pre-determined mesh size, and the particles that fall through the mesh are used in the process. In order to get an increased amount of silica gel in the composite, a HDPE with a high melt flow is utilized. This allows for the HDPE to melt together more, and therefore providing a matrix that allows for more silica gel, albeit with a higher pressure drop. Once the HDPE and silica gel are added to each other, they are mixed for a certain amount of time that allows for adequate mixing.

A putative mechanism poses that the ascorbic acid is associated to the silica through water mediated bonds. Water is necessary for the reaction to occur at a sufficient level to achieve a quantitative conversion of $NO_2$ to NO. Based on the pore size tests of various silicas, a pore size of about 40-80 Å, about the size of one to two ascorbic acid molecules, is necessary for maximum conversion capability. It appears that the ascorbic acid is being bound on the surface of the silica in a way that activates it for conversion. This may be due to the nucleophilicity of the silica mediated by the bound water to enhance the ability of ascorbic acid to give up protons to $NO_2$, creating a rapid, concerted reaction to form NO. Sodium ascorbate does not convert $NO_2$ to NO, which supports the putative concerted reaction mechanism.

Water also enhances the ability of silica-bound $NO_2$ to move through the cartridge to ascorbic acid, thus increasing the NO output and increasing cartridge efficiency. This water would not be directly associated with the ascorbic acid, but just the silica. Too much water in the input gas flow to the cartridge, identified by active condensation on the surface of the cartridge, can dissolve and wash away ascorbic acid, providing gas paths that have poor to no conversion ability and results in early cartridge failure. Also, too much water on an anaerobically sealed cartridge over time, results in an anaerobic degradation of ascorbic acid which generates $CO_2$ and decreases the conversion capacity of the cartridge. So, the stored cartridges should have moisture, yet should be reasonably dry to maintain shelf-life, though work is ongoing to optimize the storage by achieving a balance between too moist and too dry.

Primary Cartridge Modules

The primary cartridge can be the specially designed composite processed with ascorbic acid. A requirement of a single primary cartridge is that it can be able to convert one complete load from a liquid vial. For safety and redundancy, two primary cartridges can be used, and they both can come from different production lots.

Composite Assembly

A composite is a porous rigid matrix consisting of a blend of silica gel and high density polyethylene (HDPE). The silica gel is intended to provide the surface structure to capture the Ascorbic Acid and moisture to initiate the conversion of $NO_2$ gas to NO gas. The HDPE is the binding material utilized to construct the rigid matrix. A sintering process is utilized to secure the structure. The composite is bonded to an upper and lower HDPE end caps and prepared for shipping/storage. The composite can be designed to have as high a percentage (70% to 85%) of silica gel as possible and still maintain mechanical integrity.

Ascorbic Acid Derivatization

The ascorbic acid solution is made using ascorbic acid and purified water. The concentration is determined using a weight to volume (w/v) method. The assembled composite is actively flushed with the solution of a predetermined concentration. (It should be noted: After the ascorbic acid solution is made, it can be used in 48 hours, and the solution can be discarded no later than 48 hours after manufacture in an acceptable manner. This is to prevent a large portion of the ascorbic acid to become dehydroxyascorbic acid, rendering it useless as an oxidizing agent). The composites are then dried to a controlled dew point.

Water has a necessary role in the function of the GeNO cartridge. Past work showed that the cartridge requires the ascorbic acid to be associated with a solid surface, with silica being the most efficient, and water is necessary for the cartridge to function. The ascorbic acid must be distributed evenly over the silica and this is achieved through dissolving it and applying it to the silica as a solution. The mix is then dried evenly to achieve a uniform distribution which does not provide preferred gas paths through the coated silica. The silica is of a size that it packs well and has sufficient separation between the beads to allow ample gas flow (~200-500 µm), yet forces the gas to have maximum access to the ascorbic acid bound to the silica.

Liquid Module

Figure 6:
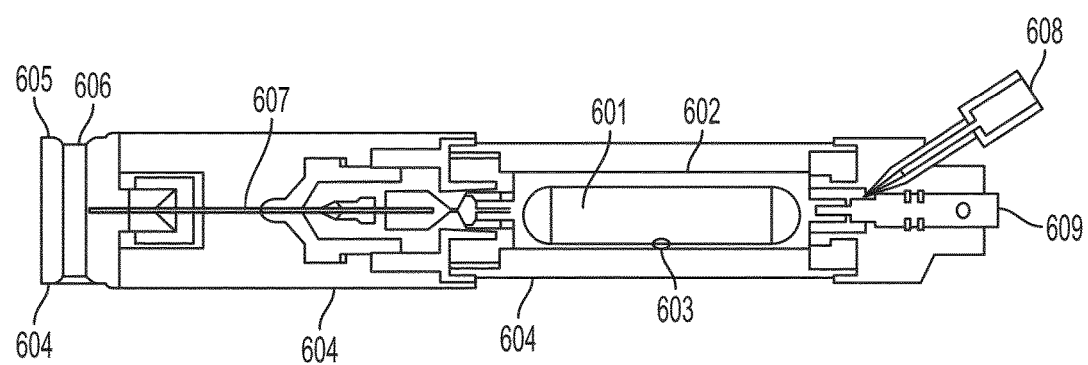
FIG. 6 is a schematic depicting a liquid module.
Figure 7:
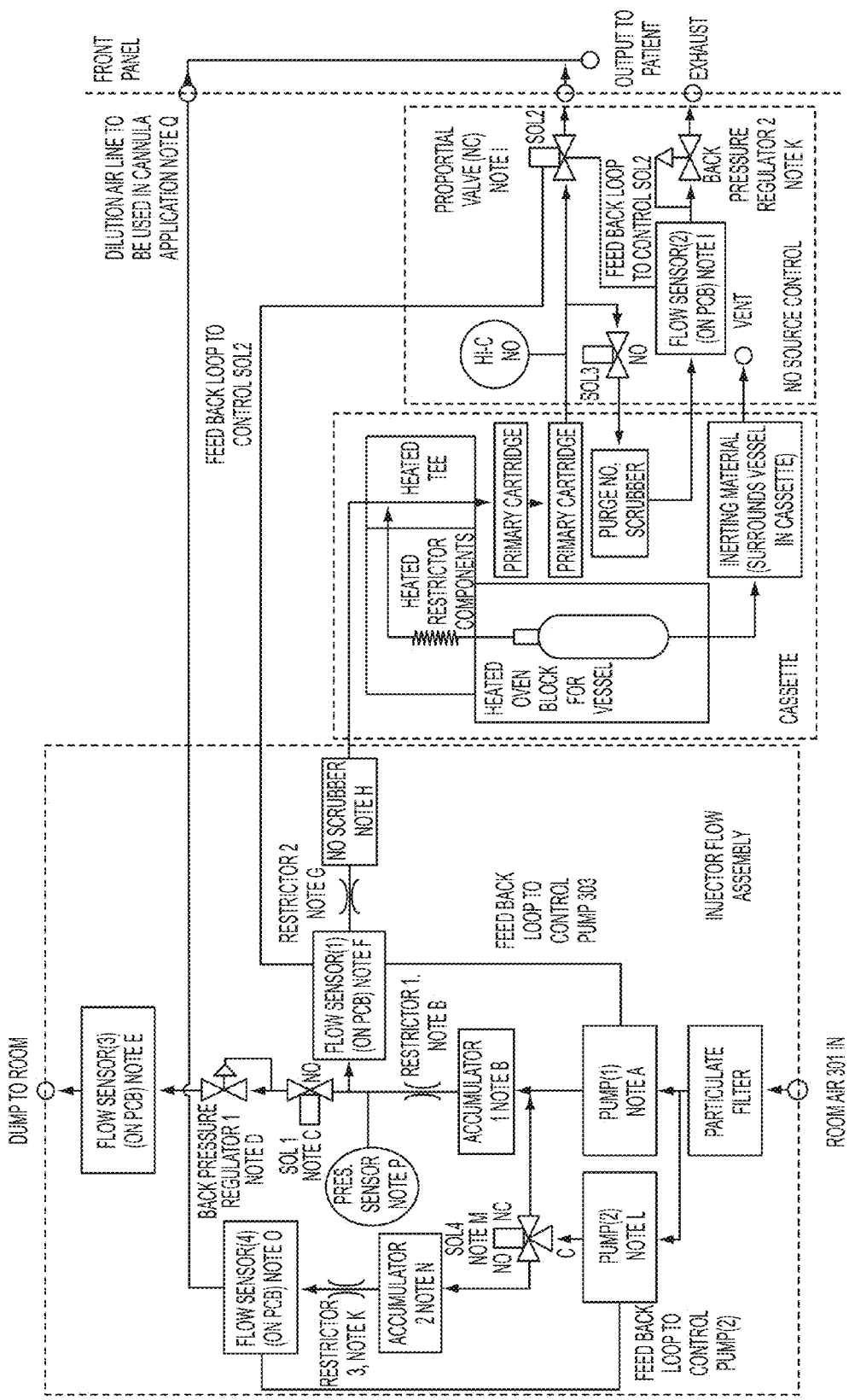
FIG. 7 is a flow diagram of supply subassembly

Referring to FIG. 6, a liquid module utilized is a sub-assembly used to store, and contain a glass ampoule 601 with liquid $N_2O_4$. The glass ampoule 601 is carried by a shuttle 602 that translates linear and rotational force to effect port closure at the distal or proximal end and effect ampoule breakage to release the ampule contents. Ampoule breakage interference feature 603. Flex heaters 604 wrap around the liquid module and restrictor column assemblies. "T"-fitting 605 is used to deliver concentrated $NO_2$ gas to flowing room air 606 across a restrictor 607 distal end. The flow restrictor 607 is a microbore glass tubing for the $NO_2$ emerging from the liquid module. A slow leak valve 608 to inerting chamber to neutralize $NO_2$ gas. Luer feature is for R&D use to determine the acceptable leak rate for design integration. Cam activation means 609 for shuttle movement can be positioned at the distal end of the liquid module.

Upon system activation (glass ampoule breakage), the liquid module can contain $NO_2$ and $N_2O_4$ gas generated when the container is heated to convert the liquid to a gas. The liquid module contains an internal mechanism to divert gas flow to either an inerting chamber or to the patient delivery plumbing of the console. It is this $NO_2$ gas generated from the liquid module that upon conversion to NO gas is delivered to the patient and controlled by the console. The liquid module is housed in the cassette that interfaces the console.

A liquid module can contain a sealed vial of $N_2O_4$ until activation of the system by the user. A liquid vial can contain a measure quantity of liquid $N_2O_4$ in a hermetically sealed glass vessel. A liquid module can provide a safe transport means for the chemical and chemical compatibility with the liquid $N_2O_4$ and $NO_2$ gas. A liquid module can provide a means to close the inerting chamber path, open the system flow path and break the ampule upon user demand. Provide a means to open the inerting chamber path and close the system flow path should Cassette be removed from the Console. A liquid module can provide a means to deliver µg of $NO_2$ in a controlled manner by temperature regulation (from the console controls) of the Liquid Module and Restrictor Assembly using flexible heating elements wrapped about the assemblies.

A liquid module can provide a means to deliver concentrated $NO_2$ gas to supplied room air to dilute the $NO_2$ gas before delivery to the conversion cartridges.

Mechanical Activation of the Liquid Module

A liquid vessel can contain the shuttle mechanism that orchestrates the gas delivery within the system. The vessel contains a shuttle feature, a heating feature and a regulator/restrictor feature.

Shuttle Feature has Multiple Performance Requirements:

A glass vial can be contained within a shuttle for shipment and storage. The shuttle can contain a feature that contains the glass vial shards from passing through the ports at either end of the liquid vessel. The shuttle can have two positions derived through shuttle rotation: shuttle can seal at either end of the liquid vessel. In one position, a gas flow can be directed to the inerting chamber and sealed to patient flow path. In another position, a gas flow is directed to the patient flow path and sealed to the inerting chamber. There can be a position where both flow paths are sealed from gas flow by single seals at either end of the shuttle but occurs at an instance in time during the shuttle rotation.

The system can be activated by rotating the shuttle to engage a feature that can result in glass vial breakage and expose the liquid $N_2O_4$ to the liquid vessel. The shuttle can be locked at the end of travel. The system should be configured that the mechanism closes the patient flow path and opens the inerting chamber before allowing for removal of the cassette. The Glass Vial should maintain structural integrity during product shipment and storage.

Heating Feature has Multiple Performance Requirements:

Wrapped about the outside of the liquid vessel can be a flexible heater that is utilized to increase or decrease the gas output of the $NO_2$ gas for patient delivery. The temperature is controlled by software within the console. Wrapped about the outside of the flow Regulator feature can be another flexible heater that is utilized to increase or decrease the gas output of the $NO_2$ gas for patient delivery. The temperature is controlled by software within the console.

Regulator/Restrictor Feature has Multiple Performance Requirements:

The regulator/restrictor is utilized in conjunction with the heaters, to control the output gas delivered to the patient delivery gas flow stream. The liquid module can create an internal pressure≥2× the pressure in the air inflow mixing T-fitting.

Access to Inerting Chamber

The liquid module inerting chamber is coupled to the liquid vessel through a controlled leak valve. The valve is intended to control the rate gas flow to the inerting material to minimize chemical reaction heat build-up that occurs as the $NO_2$ gas is neutralized.

The shipping and shut-off design/configuration position of the shuttle can expose the Liquid Vessel chamber to the Inerting port and seal-off the patient delivery port. Should glass breakage occur during product shipment, it is intended for the device to contain the hazardous NO2 gas by diverting it to the Inerting Chamber to neutralize the gas.

A Supply Subassembly

A supply subassembly of a nitric oxide delivery system can include a cassette module, cartridge(s) and a liquid module. The system includes a control subassembly, a NO supply subassembly, and a sample sensor subassembly. The control subassembly includes a computer system with small integral display, a battery for backup, an application specific PCB (heater control, solenoid control, switches, battery charger, analogue input, etc.), and a computer memory storage system. The NO supply subassembly includes 1) a cassette including a heated vessel, primary cartridges, an inerting material, a purge scrubber, a restrictor, and a housing, 2) an injector flow module including a flow sensor, pumps, a flow restrictor, a scrubber, a particulate filter, an air dump back pressure regulator, and a pump backup solenoid, and 3) a NO source control including a proportional valve, a purge solenoid, a purge flow sensor, a purge back pressure regulator, and Hi-C NO sensor. The sample sensor subassembly includes a sample/calibration solenoid, a permapure drier, a sample flow module (including a flow meter, a flow restrictor, and a pump), a water trap (external) and a pressure transducer, a sensor subassembly (NO, $NO_2$ and oxygen sensors and sensor control PCB, and a $NO_x$ scrubber.

Referring to FIG. 7, this shows the flow scheme of the supply subassembly. The room air is introduced to a particulate filter and can flow into two pumps (FIG. 7, Pump (1 ) and Pump (2)). Pump (1) is capable of flows up to 1 L/min at 5 PSI or greater, which can satisfy all ventilator and some cannula applications. Pump (2) can be used to supply dilution air to achieve the higher cannula flows when required. For the ventilator application, flow from 0.2 to 1.0 L/min can be required. These pumps typically do not have this large, i.e. 5×, dynamic range without stalling out at the lower flows, thus the need for Back Pressure Regulator 1. Under typical ventilator operation, the proportional valve, Sol 2 sets the output flow, which is also the flow measured by Flow Sensor (1). If the pump is sets to the lowest acceptable flow, which exceeds the desired output flow, the excess is automatically exhausted through regulator (1) into the room. Since this in only air, it is acceptable to exhaust this gas. Since Pump (1) has been chosen to achieve flows up to 1 L/min for the ventilator application, and since at time flows as high as 4 L/min may be required for the cannula application, Pump (2) has been added as a "dilution" pump. Pump (2) most likely could be identical to Pump (1) since Pump (1) is required to supply 1 L/min at pressure of greater than 5 PSI, while Pump (2) is operating at nominal atmospheric pressure, thus it may be able to achieve 3 L/min at nominal 0 PSIG.

Accumulator (1) along with a restrictor can be used to dampen out the pulsations from the diaphragm pump. It is desired to have a steady and not pulsating flow through the rest of the system. Note that Restrictor 1 must be significantly less restrictive than Restrictor 2. Accumulator 2 and Restrictor 3 can be used to dampen the pulsations from the diaphragm Pump (2).

Flow Sensor (4) is used to determine the dilution flow from Pump (2) that mixes with the Acute output. The total flow to the patient is the sum of the flows of Flow Sensor (1) and (4). Based upon the flow set point the software can determine the actual ratio of the flows from Pump (1) and Pump (2). This is an optional pressure sensor. It would be used to confirm that Back Pressure Regulator 1, when Sol 1 is open, is set properly. Under all conditions, i.e. Sol 1 activated or not, it measures the pressure of the pump, which is a measure of the pump performance. Knowing the pump operational voltage, the output flow and pressure can be used to determine if there is any degradation of the pump, and give an early warning signal to replace the pump before failure.

Other Exemplary Embodiments

An $N_2O_4$ liquid based system can be used to deliver inhaled nitric oxide (NO). The delivery system can be intended to be used in conjunction either with a ventilator or a cannula. The liquid $N_2O_4$ boils off as $NO_2$ (gas), since in liquid form $NO_2$ can be present as the $N_2O_4$ dimer. The $NO_2$ can then be converted into NO using at least one converting cartridge. The amount of NO presented to the patient can be varied by changing the temperature of the $N_2O_4$ liquid reservoir, and thus the vapor pressure above the liquid, by the choice and temperature of the restrictor column, and by the settings of the scrubbed by-pass air flow if used. The NO concentration can be controlled via a feedback loop from the NO sensor monitoring the NO in the patient ventilator or cannula line, just prior to the patient. This feedback loop can control the liquid and restrictor temperatures and the flow through the scrubbed by-pass system if the scrubbed by-pass system is active. A console will provide NO concentrations from 1 to 40 PPM with ventilator flows between 2 to 20 LPM for the ventilator application, and 10 to 80 PPM at output flows of 0.5 to 4 LPM for the cannula application. A secondary $NO_2$ to NO converting cartridge will be placed just before the patient. This secondary cartridge will remove any residual NO2 that may have been formed in the delivery gas plumbing, thus ensuring that the ventilation or cannula gas presented to the patient has an $NO_2$ concentration of virtually zero.

Figure 8:
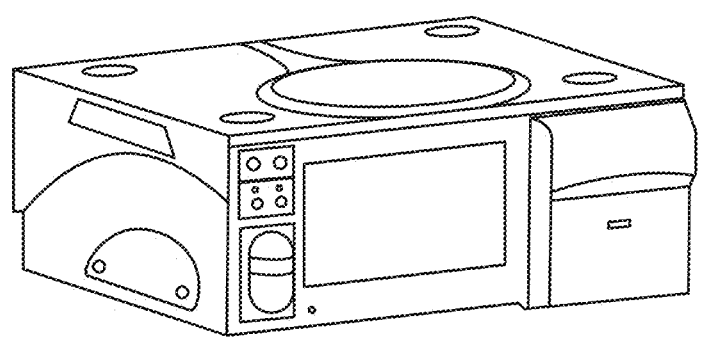
FIG. 8 is an exemplary console.

Referring to FIG. 8, in one embodiment, a system (such as the GeNOsyl Acute DS) can be comprised of 1) a primary console, 2) an identical, fully-functional backup console (required for the ventilator mode, optional for the cannula modes), 3) one cassette per console, and 4) external tubing and accessories. A system can include both the primary console and the backup console. Failure of a system can include the inability of both the primary and backup consoles to deliver NO at the desired set point.

Figure 9:
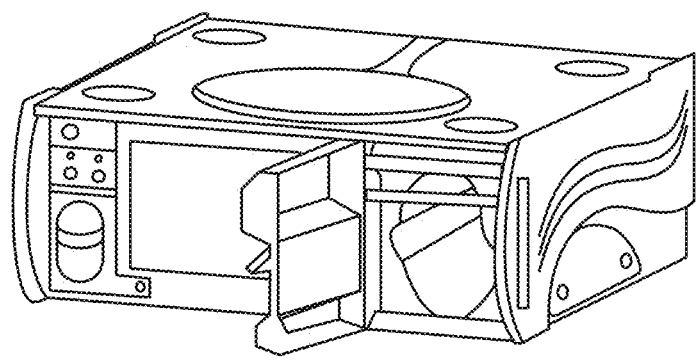
FIG. 9 depicts an exemplary console.

Referring to FIG. 9, the figure shows an exemplary GeNOsyl Acute DS Console with Cassette door OPEN and displaying 3-position activation lever.

A system can be a hospital-based nitric oxide (NO) delivery system that can deliver controlled doses of inhaled NO for diagnostic or therapeutic purposes to a patient in conjunction with a ventilator system or direct through a nasal cannula.

A delivery system can be used in several configurations. The ventilator configuration can be used with a face mask in conjunction with a ventilator for therapeutic use. The cannula configuration can be used with a nasal cannula or a face mask for both therapeutic and diagnostic applications. A console can includes a single cassette, which can incorporate liquid $N_2O_4$, and a pair of $NO_2$ to NO converting cartridges (primary cartridge).

Upon initiation of the console, the liquid $N_2O_4$ can be heated and can convert to $NO_{2(gas)}$. The $NO_2$ can then be converted into NO using $NO_2$ to NO converting cartridges and delivered to the patient in conjunction with a ventilator system or direct through a nasal cannula or face mask. The amount of NO presented to the patient can be varied by changing the temperature of the $N_2O_4$ liquid module. The NO concentration at the patient can be controlled via a feedback loop from an NO electrochemical sensor, which can monitor the NO in the patient ventilator line or cannula line. The NO sensor output can be compared to the demand NO concentration (NO concentration set point chosen by the user) by the control circuitry which in turn can adjust the liquid module temperature.

Figure 10:
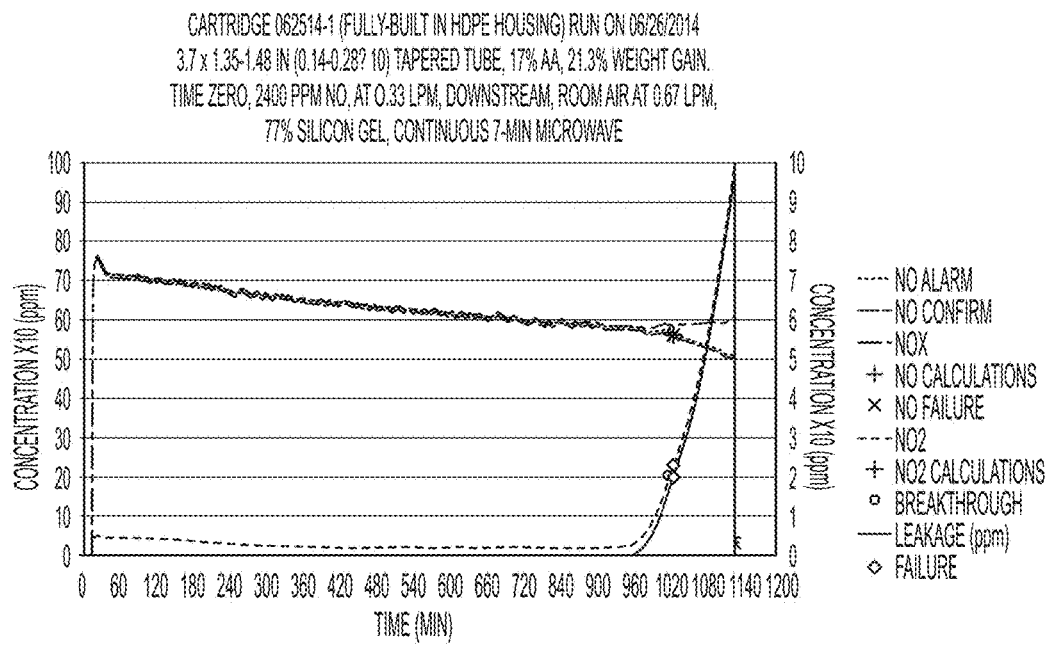
FIG. 10 shows an exemplary output performance curve.

Referring to FIG. 10, the figure depicts an exemplary output performance curve. NO concentration delivered to the patient can range from about 0.1 PPM NO with a ventilator flow of 2 LPM to 20 PPM at 10 LPM (nominal, up to 40 PPM under extreme conditions with reduced Cassette lifetime). The system operates with an optional humidifier placed after a cartridge, for example, a secondary cartridge. A secondary cartridge can convert any residual $NO_2$, or $NO_2$ formed due to line conversion, to virtually zero. A secondary cartridge can be placed before any humidifier so as to prevent condensation from forming in the cartridge.

GeNOsyl™ Acute DS Cannula System

The GeNOsyl™ Acute DS, may only provide a tiny fraction of the input volume of a breath, the rest being made up of room air (entrained air). The GeNOsyl™ Acute DS can control the concentration of the NO at the cannula. One advantage of the GeNOsyl™ Acute DS as compared to using a gas tank may be that for the DS, both the flow and the concentration can be varied, whereas when using a gas bottle only the flow rate can be varied.

GeNOsyl™ Acute DS Ventilator System with Secondary Cartridge

For the GeNOsyl™ Acute DS both the output flow and the output concentration are variable. In order not to affect the ventilator controls, the output flow of the GeNOsyl™ Acute DS can typically be limited to no more than about 10% of the total flow from the ventilator. Since the NO output of the console can be controlled by the temperature, and varying the temperature can change the mass of NO supplied per minute, it can be the temperature of the vessel that determines the mass delivered to the patient.

Cassette

When a cassette is inserted into a console and activated, for example, by breaking the cassette seals, the two parts of the cassette interact to control the dose of NO gas delivered to the patient. A cassette can be a self-contained disposable product that can be inserted into a console (for example, the GeNOsyl Acute DS Console), which can be externally coupled with a secondary cartridge to form a system, for example, the Acute DS System.

Figure 11:
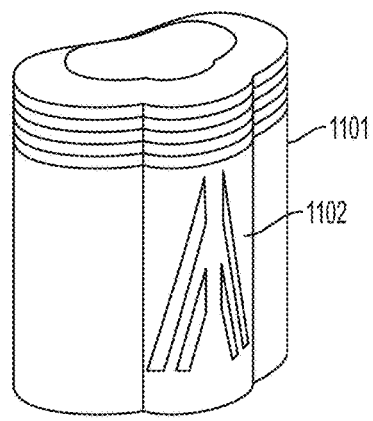
FIG. 11 shows a cassette.

Referring to FIG. 11, a cassette 1101 can include various modules that produce and convert the NO gas delivered to the patient. The cassette and cartridges can be disposable modules that also provide user and environmental safety features and indicators. For example, a cassette 1101 can be a self-contained disposable cassette with a viewing window 1102, such as a color change inerting material viewing window for example, that is configured to render the cartridge safe for disposal.

A cassette can include three discrete subassembly modules.

Liquid Module Assembly

Figure 12:
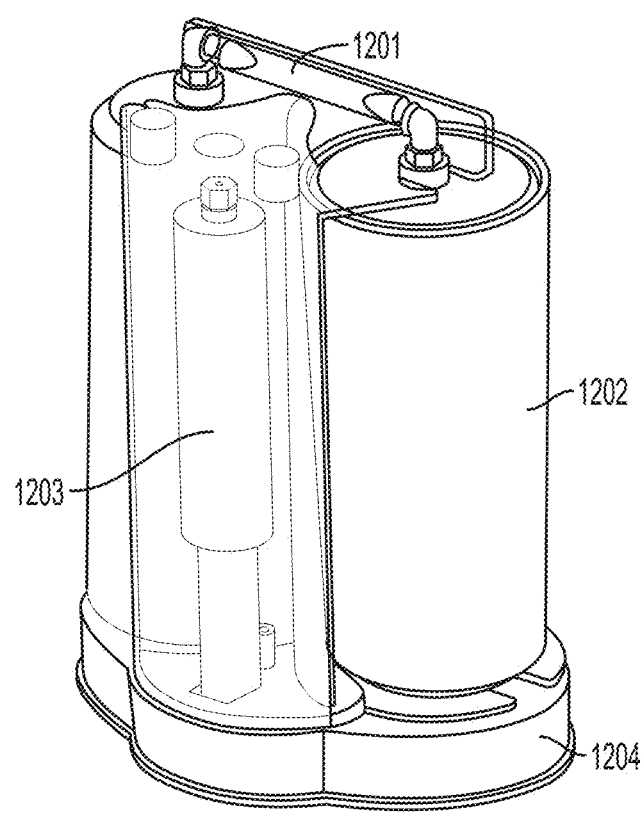
FIG. 12 shows a cassette assembly.

Referring to FIG. 12, a cassette assembly can include a liquid module assembly 1203, a cartridge 1202, a cartridge bridge tubing 1201, and a base 1204. The liquid module assembly can contain and control the integrity of the $N_2O_4$ holding vessel. A holding vessel (also referred to herein as a liquid vessel) can include one or more components for breaking the glass seal and heating the $N_2O_4$ to activate the liquid, temperature controls to generate and maintain vessel pressure, and one or more components for directing gas flow to either an inerting chamber or for delivery to the patient. A liquid module assembly can also include a $NO_2$ flow regulator to meter $NO_2$ from the holding vessel to the air stream used to carry the $NO_2$ through the gas circuit for conversion into NO. To provide added safety from $NO_2$ exposure to the user in the event of an accident or misuse, the $N_2O_4$ liquid chamber can be encased in an inerting material. There can be also a hermetic barrier to contain the $NO_2$. The inerting material can initiate a color change indicator to alert the user that $NO_2$ has been discharged into the inerting chamber.

A liquid module assembly can be a sub-assembly used to store and contain the liquid $N_2O_4$. Upon system activation (glass ampoule breakage), the liquid module assembly will contain $N_2O_4$ and $NO_2$ gas generated when the container can be heated to convert the liquid to a gas. The liquid module assembly can contain the internal mechanism to divert $NO_2$ gas flow to an integrated self-contained inerting chamber or directed towards the flow restrictor for discharge to a cassette circuit to convert the $NO_2$ gas to NO. It can be this NO gas generated through a cassette that can be delivered to the patient and controlled by a console. The liquid module assembly can be housed in a cassette that interfaces a console.

The liquid module assembly can incorporates temperature controls that effectively control the NO2 gas pressure and a restrictor to control the rate of release of $NO_2$.

The liquid module assembly can operate in a manner to permit $NO_2$ gas flow to the primary cartridge OR to the inerting chamber. The mechanism may make it impossible for both valve seals to be open simultaneously.

Figure 13:
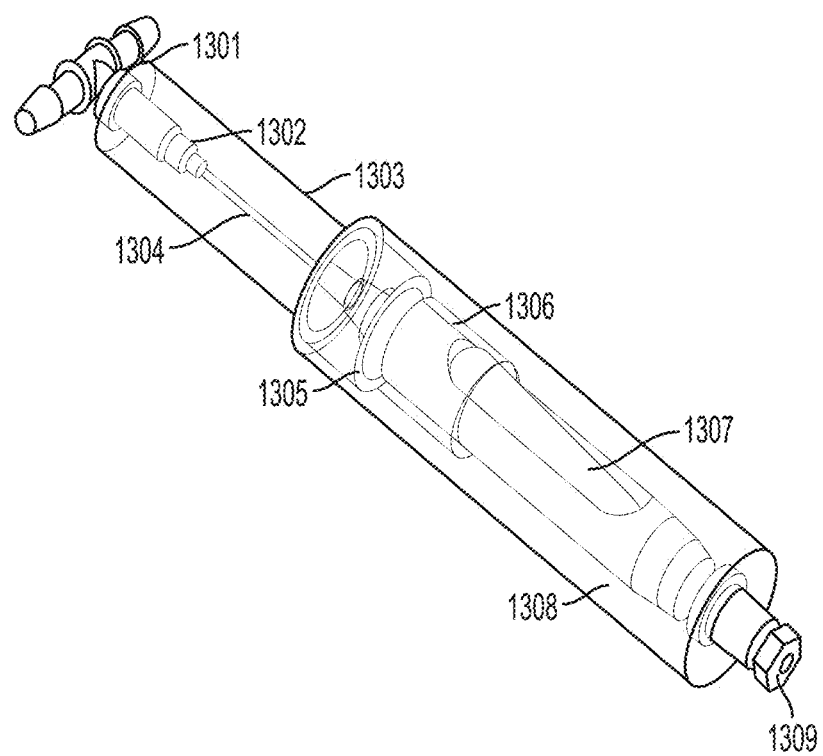
FIG. 13 shows a liquid vessel and restrictor assembly.

Referring to FIG. 13, a liquid vessel and restrictor assembly can include a glass ampoule 1307 with $N_2O_4$, metal liquid vessel 1308 with flex heater, shuttle 1307 and slow leak valve 1309 and seals, restrictor column 1304, metal restrictor housing 1303, with flex heater & tee fitting 1301, ferule 1302, an optional crush Teflon O-ring 1305, and heaters wrap the restrictor housing and liquid vessel (not shown).

Figure 14:
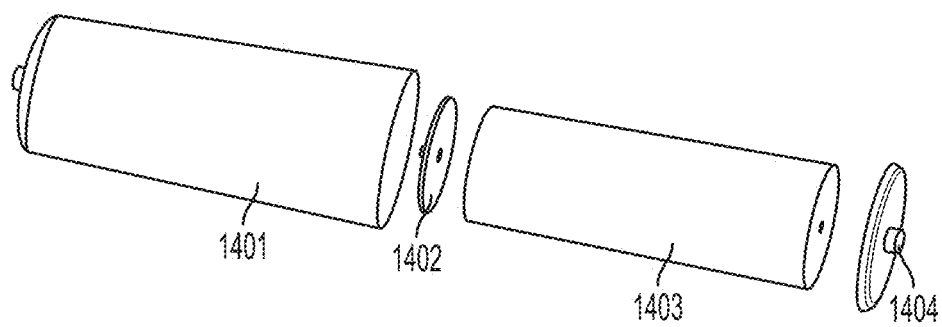
FIG. 14 depicts cartridge components.

Referring to FIG. 14, cartridge components include a primary cartridge housing 1401, a composite inlet cap 1402, composite 1403 (silica gel/HDPE) and composite outlet cap 144.

$NO_2$ to NO Conversion Cartridges

Figure 15:
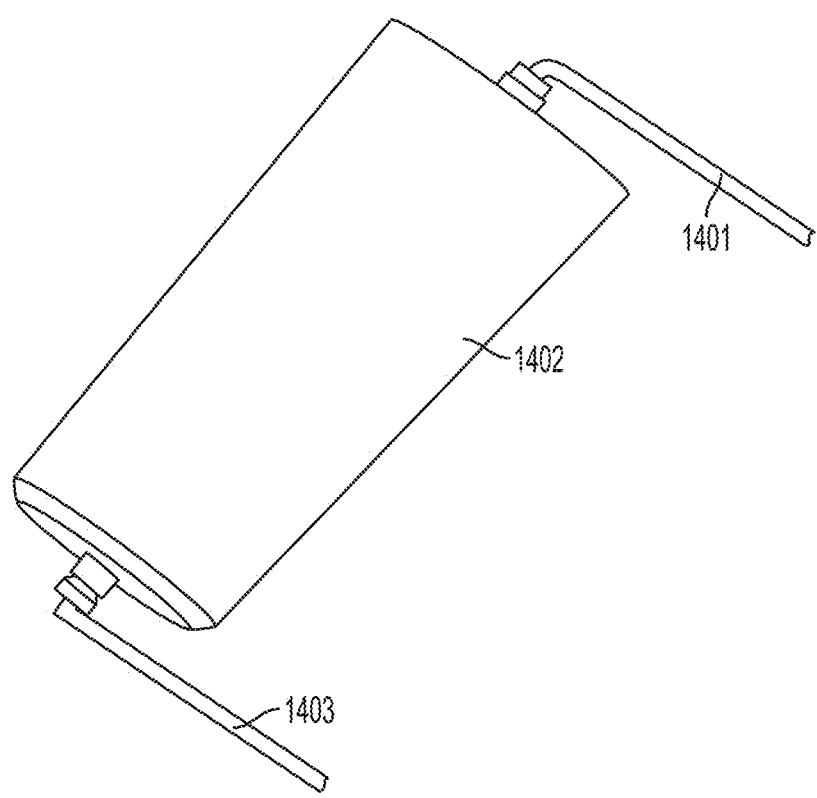
FIG. 15 shows cartridges in an assembly.
Figure 16:
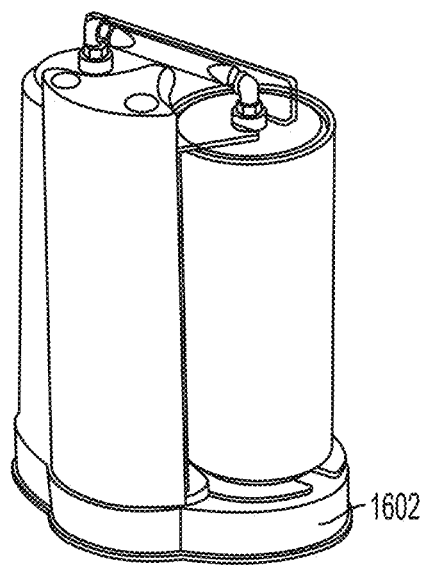
FIG. 16 shows a cartridge mounted on a base.

A cassette can contain two independent $NO_2$ to NO conversion Cartridges. Referring to FIG. 15, each cartridge can include a cartridge outlet 1501, a primary cartridge housing 1502, and a cartridge inlet 1503 thereby forming a cartridge assembly, and can be capable of converting the entire capacity of the $N_2O_4$ liquid supply, with a >25% additional capacity. Two or more cartridges can be able to convert $NO_2$ to NO gas, with a safety factor of >150%. The system can be designed to operate safely and effectively with one of the two cartridges being absent. Referring to FIG. 16, the cartridge can be mounted to a base 1602.

A primary can be contained within a cassette to convert $NO_2$ gas into NO gas. A cassette can contain one or more primary cartridges. If the cassette includes two or more cartridges, the cartridges can be in series to provide double conversion redundancy before delivery of NO gas to the patient. This conversion can be accomplished through a reaction of $NO_2$ gas with a reducing agent included in the composite matrix. Gas flows through the coated composite in a torturous path created by the composite matrix to effect the conversion.

A composite can be a porous rigid matrix including a blend of silica gel and high density polyethylene (HDPE). The HDPE can be the binding material utilized to construct the rigid matrix. A thermal sintering process can be utilized to secure the structure.

Primary Cartridge Modules

A primary cartridge can be composite processed with ascorbic acid. A single primary cartridge can convert the entire fluid contents of the vial with >25% excess capacity. For safety and redundancy, two primary cartridges can be used.

Composite Assembly

A composite cartridge can be a porous rigid matrix. The porous matrix can include a blend of silica gel and HDPE binder material. The silica gel provides the surface structure to capture the reducing agent, for example, ascorbic acid, and moisture to initiate the conversion of $NO_2$ gas to NO gas. The binding material can be utilized to construct the rigid matrix. The composite can be secured within the housing for stability in shipping/storage. The composite can be designed to have as high a percentage of silica gel as possible and still maintain mechanical integrity.

Ascorbic Acid Derivatization

The assembled composite can be actively flushed with a known solution of ascorbic acid dissolved in water. (Note: it can be important that oxygen be excluded to minimize the conversion of ascorbic acid into dehydroxyascorbic acid.)

Water can play a role in the function of a cartridge. A reducing agent can be distributed evenly over the porous matrix, and this can be achieved, for example, through dissolving it and applying it to the porous as a solution. The mix can then be dried evenly to achieve a uniform distribution, which does not provide preferred gas paths through the matrix including. The porous matrix can be of a size that it packs well and has sufficient separation between the particles to allow ample gas flow, yet forces the gas to have maximum access to the reducing agent (e.g., ascorbic acid) bound to the porous matrix.

Cartridge Assembly

Upon completion, the treated composite assembly can be assembled to an outer housing, sealing it from the environment. A cartridge housing can have an extremely low permeability to moisture and oxygen, or be packaged such to minimize permeability to moisture and oxygen. Although the cartridges can be packaged with the cassette, it can be important to use materials that provide adequate resistance to moisture and gas. In one embodiment, the two cartridges in each cassette can be made from different manufacturing process lots for safety redundancy.

Cassette Housing Assembly

A cassette housing assembly can contain a structural base to which other cassette components can be mounted, including two Schrader valve-like assemblies to provide independent gas flow, the outer housing with the inerting material, preferably color changing inerting material visible), and a tamper evident strip, which can shroud the cassette inlet and outlet ports.

Figure 17:
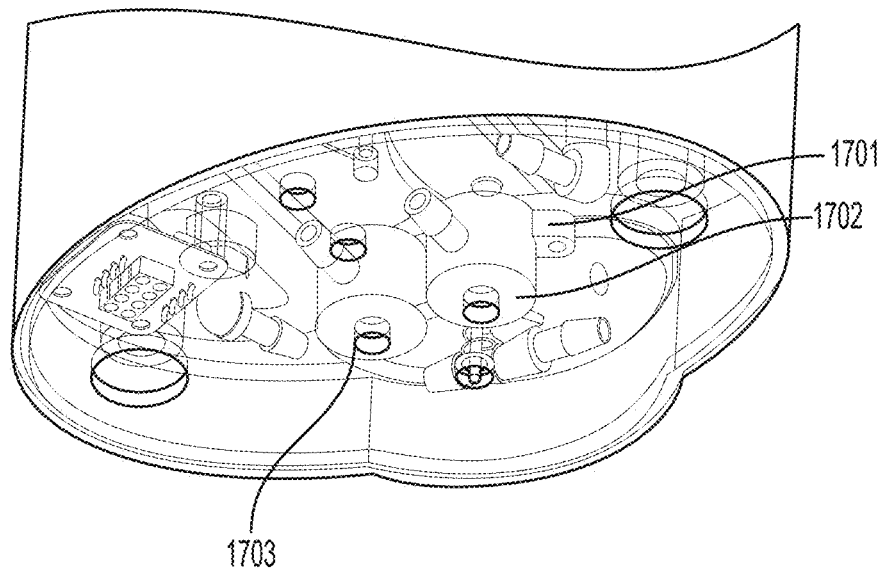
FIG. 17 shows a cassette base manifold.

Referring to FIG. 17, the cassette base manifold can include a Schrader-like valve assembly 1701, an air IN access port 1702, and Air NO/OUT Access port 1703, and a foil seal 1704, which covers ports (not shown). The cassette base can provide access to the following system functions:

Air $_{IN}$ access through a Schrader-like valve assembly.

Air/$NO_{OUT}$ access through a Schrader-like valve assembly.

Activation Rod access through small access port (non-accessible activation by the user).

$NO_{IN}$ gas purge/scrubber access.

$NO_{OUT}$ gas purge/scrubber access.

Heater(s) and temperature sensor(s) electrical contacts exposed for INACTIVE STANDBY mode (all passive components).

Tamper evident foil seals over access ports (except electrical contacts).

Tamper evident foil seal breakage provides a mechanical "lock-out" for Cassette reuse.

Figure 18A:
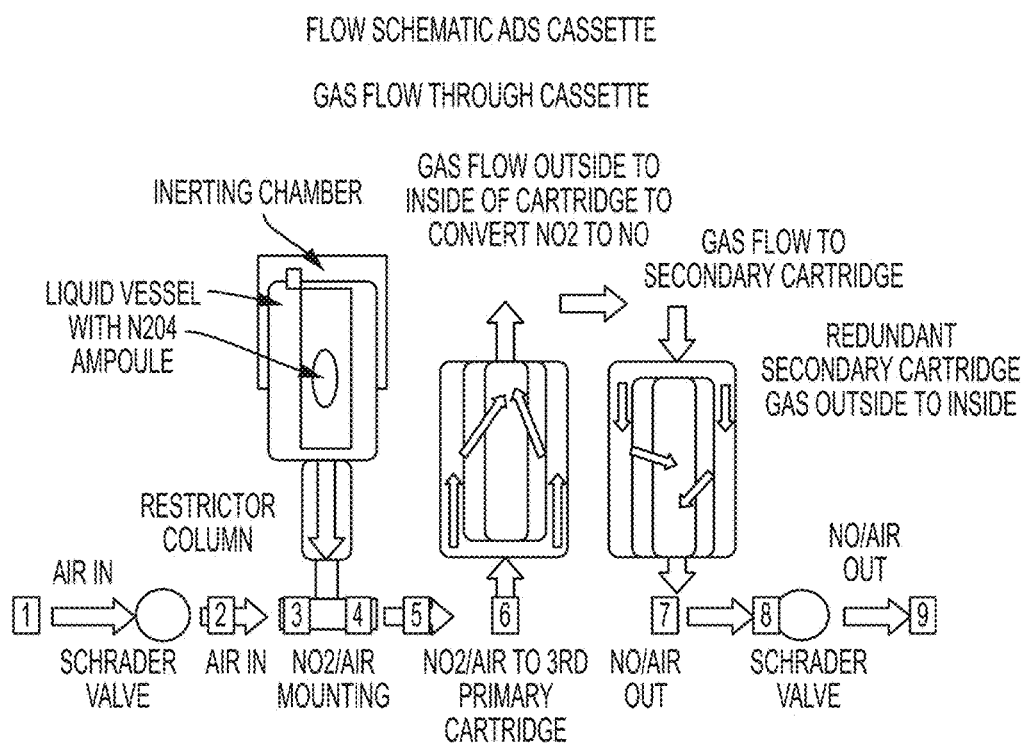
FIG. 18A shows a gas flow bath showing the exit locations on the base.
Figure 18B:
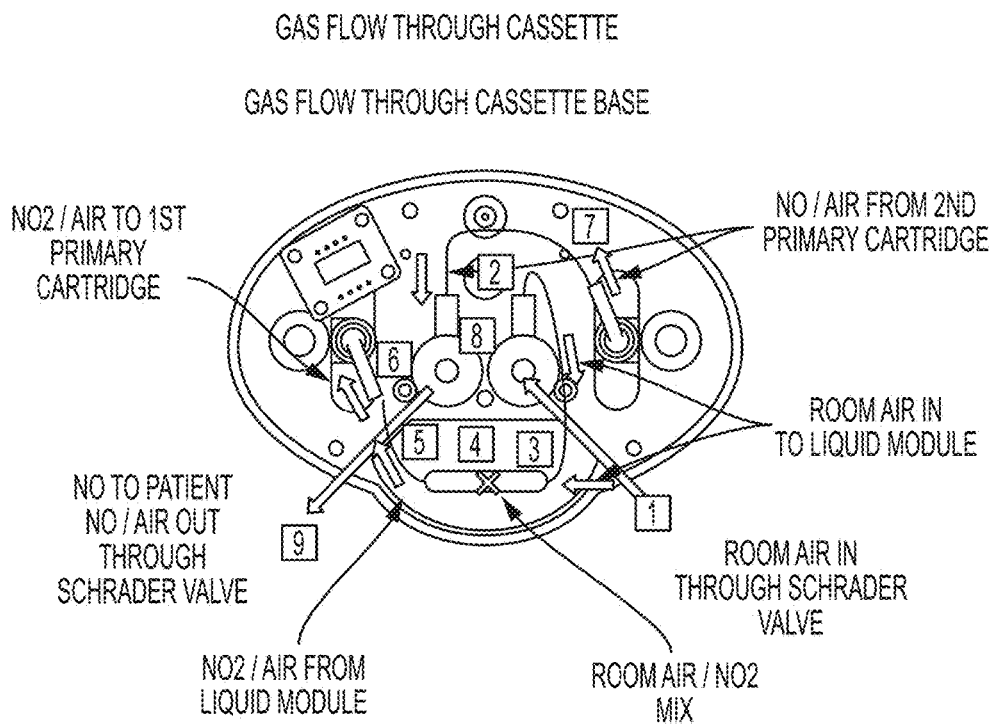
FIG. 18B shows the exit locations from FIG. 18A.

Referring to FIGS. 18A and 18B, these show the gas flow details of one cassette embodiment. FIG. 18A shows a gas flow bath showing the exit locations on the base. FIG. 18B shows the exit locations from FIG. 18A. The numbers in the square box on the two figures refer to positions and are described below:

1. The gas flow intake from the console can be our own specially designed Schrader valve. It can use a ball and a spring to seal, and can be shown in more detail in FIG. 12.
2. The incoming air flow can be piped to a T fitting.
3. The incoming air can pass through the T fitting. Inside the T fitting, the air can combine with NO2 coming from the liquid vessel. The flow out of the liquid vessel can be controlled by the upstream pressure in the vessel, which can be controlled by the temperature of the liquid. The flow rate can be defined by the pressure drop through the restrictor tube.
4. Air containing the NO2 can exits from the T fitting.
5. The air/NO2 mixture can leave the T fitting on its way to the first ascorbic acid cartridge.
6. The air/NO2 mixture can enter the first ascorbic acid cartridge. The flow can be forced to the outside of the cartridge and it can exit out the center of the cartridge. The cartridge itself can have a small taper to allow it to be molded without the need for chemicals to release the cartridge from the mold. The gas leaving the cartridge at the top of the figure may now contain a mixture of air and NO. The gas can then enter the second redundant cartridge.
7. The air/NO mixture can exit from the second cartridge.
8. The air/NO mixture can enter the second Schrader valve.
9. The air/NO mixture can exit from the cartridge.

The cassette design can assure that the $NO_2$ remains inside the cassette and never leaves the cassette.

Figure 19:
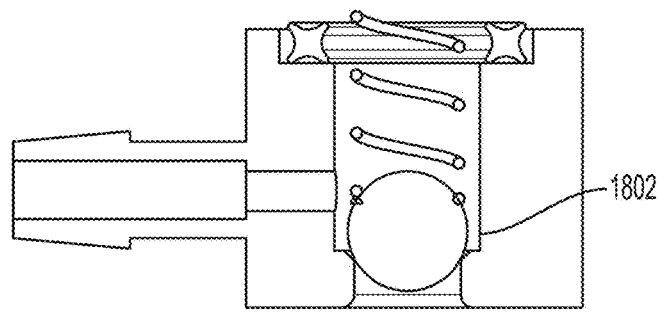
FIG. 19 shows a cross-section of a Schrader-like valve.

Referring to FIG. 19, this shows a cross-section of a Schrader-like valve with a spring loaded ball 1802, normally closed. The ball is opened when inserted into the console.

A cassette can be fully integrated, single use disposable and interfaces to a console. A cassette can be activated via the interface lever on the console which causes a console mechanism to engage the cassette, break the glass ampoule and initiate NO delivery to the patient.

A cassette can provide adequate design safety features listed below to limit $NO_2$ exposure to the equipment, user, patient or shipping carrier:

i Glass Ampoule

Volume of $N_2O_4$ contained in a cassette can be within the safe EPA/FDA/DOT limit.

ii Shuttle Seals

The $N_2O_4$ can be contained in a hermetically sealed glass ampoule that can be positioned in a plastic shuttle mechanism that (upon opening) can permit $NO_2$ gas flow to either enter an inerting chamber or be directed out to the patient. The seals can all be doubly redundant.

iii Inerting Chamber

The cassette can be shipped with the glass ampoule exposed to the inerting material that would render the $N_2O_4/NO_2$ gas inactive should the glass ampoule break in shipment. The inerting material can undergo a permanent color change if exposed to $N_2O_4$. $NO_2$ liquid and the color change can become visible through the cassette window. This provides the user with an indication that the cassette may no longer be functional and should probably not be used.

iv Slow Leak Valve

In the event that the glass ampoule breaks prematurely, the gas flow rate into the inerting chamber can be controlled, for example, to manage reaction temperature build-up and provide adequate time for the inerting reaction to occur.

v Schrader-Type Valves Sub-Assembly and Ports

All high concentration $NO_2$ gas plumbing can be contained within the cassette, thereby entirely eliminating environmental exposure to $NO_2$ from a leak.

Both the air inflow and NO/Air gas outflow ports can provide back-up seals independent from the liquid vessel shuttle mechanism in case of an outlet seal failure. These ports can have spring loaded automatically closing Schrader valve.

vi Tamper-Evident Seal(s)

The base of the cassette can contains a foil seal covering the inflow and NO gas outflow Shrader valves. These seals may be punctured upon system activation to provide visual indications that the cassette has been used as well as to provide a tamper evident seal from the user inadvertently challenging the Schrader seals.

vii Purge/Scrubbing Material

The cassette can also contain a purge/scrubbing material which can be used to scrub low level NO gas emerging from a console during priming of the system, and as a bypass during very low NO delivery concentrations.

viii Cassette Construction

The cassette housing can be capable of withstanding internal pressures that are 50% higher than can be generated during performance.

ix Shipping Packaging of the Cassette

The cassette packaging can be a clear container, such as a thermoform tray, that provides product integrity during shipping/transportation handling as well as providing the user the ability to visualize the inerting chamber for color change (should the glass ampule break in shipment).

Figure 20:
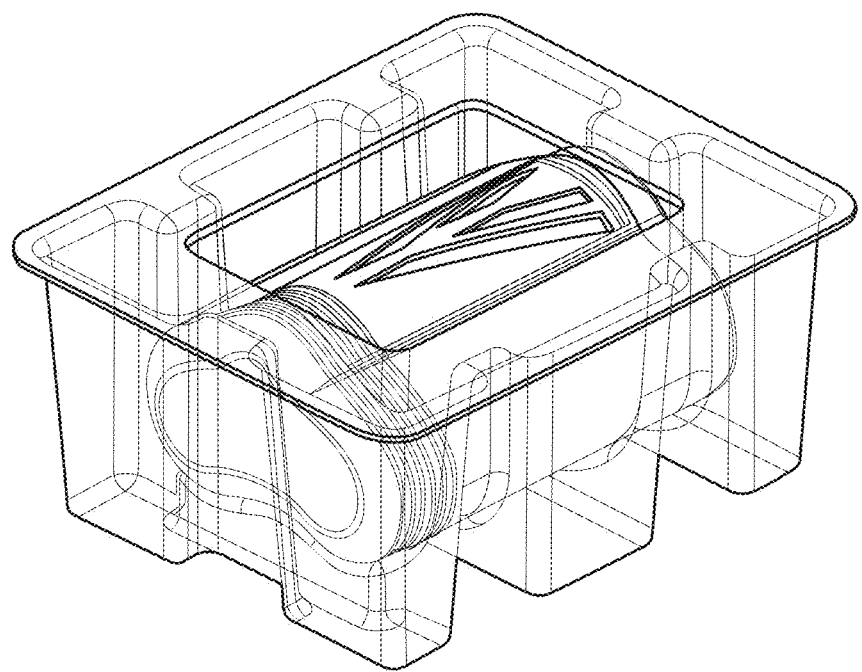
FIG. 20 shows an exemplary cassette packaging.

Referring to FIG. 20, this shows an exemplary cassette packaging.

A cassette can include two major systems: a) liquid module and b) conversion cartridges. The two systems can be independent but function symbiotically to convert liquid $N_2O_4$ to NO gas within the unitized housing. A cassette can interface to the console, which can provide the necessary electronic, software and mechanical controls to control the delivery of the desired NO/Air gas dose to the patient, delivered in the low parts per million (PPM) concentration range.

The design can include a variety of safety features that provide environmental protection to the user. These safety features can be consequential to the mechanism design but the intent of these safety features is generally to reconcile the potential harmful consequences of unintended failures that could possibly occur.

Figure 21:
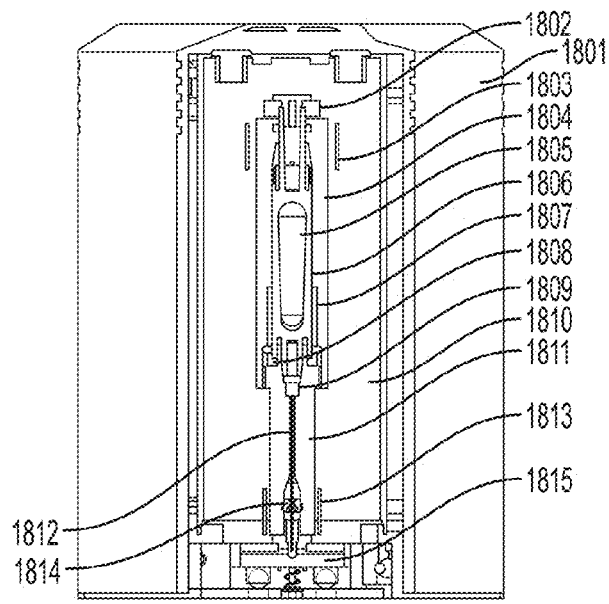
FIG. 21 shows a cassette base assembly.

Referring to FIG. 21, a cassette base assembly can include a cassette housing 1801, a slow leak valve 1802 (optional design), 1 liquid vessel heater 1803, a liquid vessel 1804, glass ampoule 1805 with $N_2O_4$, a shuttle 1806, an ampoule crush feature 1807, Teflon crush washer 1808, a sintered filter 1809, restrictor housing 1811, restrictor column 1812, a restrictor column heater 1813, ferule 1814, and tee fitting 1815.

Liquid Module

A cassette can provide containment for liquid $N_2O_4$. Liquid $N_2O_4$ can be the primary component that when released and purified and its flow controlled, can result in known amounts of inhaled Nitric Oxide (NO).

The liquid $N_2O_4$ may be contained in variety of containers of which one method can be to dispense the liquid into an onion skin glass ampoule that can then be hermetically sealed, for example, by means of a hot flame. The glass ampoule can resemble a capsule approximately 0.28 inches in diameter and 1.25" long with 0.0025" wall thickness. The diameter and wall thickness can be an industry standard glass ampoule and could have other shape features and dimensions. The $N_2O_4$ fill volume can be less than 0.52 ml, which provides about one day's supply of NO gas during normal use.

A glass ampoule can include a number of features:
a) It can be clear, which can permit visualization in-process of the fill volume;
b) It can provide a hermetically sealed environment for the contents and can render it independent of environmental conditions, such as temperature, humidity, etc.
c) It can provide a breakable container for on-demand activation;

The design can provide mechanical and thermal features to expose the contents of the glass ampoule to allow conversion of the $N_2O_4$ liquid to $NO_2$ gas, and then regulate the $NO_2$ gas flow. This can be accomplished within the liquid module.

The heart of the liquid module can be the liquid vessel and the restrictor housing assembly.

A liquid vessel can be cylindrical in shape with performance functions at each end. Although shape may be not a controlling attribute, the purpose can be to provide two distinct operating modes within the device: a) delivery of $NO_2$ gas out of the liquid vessel towards the patient delivery conduits, or b) delivery of $NO_2$ gas to an inerting chamber for neutralization. To accomplish this, a shuttle mechanism can be incorporated into the liquid vessel. The shuttle can move between two end positions activated by a linkage from the console control. At one end of a liquid vessel can be a port that leads to patient flow conduits. At the opposite end can be a port that leads to a hermetically sealed inerting chamber contained within a cassette. In between, the two resting positions of the shuttle through an interference feature that upon initial activation compresses and fractures the glass ampoule (to release the $N_2O_4$).

A shuttle can be housed within the liquid vessel, which can be made of metal, for example, stainless steel or titanium. A shuttle can contain a feature to safely hold and stabilize a glass ampoule. In its shipping position to the customer, a shuttle can be positioned such that the inerting chamber port can be open to gas flow from the liquid vessel (which also results in the patient flow port being closed). This condition can be for safety should the glass ampoule break in shipment or handling, any $N_2O_4/NO_2$ that escapes from the broken glass will be exposed to the inerting material to neutralize it.

The activation of the system can only occur after the cassette can be placed within the console. This can occur via an activation rod (controlled within the console) that can shift the position of the shuttle from inerting chamber open/patient flow port closed to patient flow port open/inerting chamber closed. Along the shuttle travel, the glass ampoule can contact an interference feature to break the glass ampoule.

Heat can be applied to the liquid vessel for the purpose of vaporizing the liquid $N_2O4$, and increasing its internal gas pressure so as to drive a known amount of $NO_2$ out of the vessel. The pressure can define the controlled amount of $NO_2$ discharged through the liquid module. Control of the temperature can function as a pressure adjustment of the release rate, for example, similar to a gas regulator does on a gas tank. In this design, flexible electrical resistance heater(s) can be wrapped about the outside of the metal housing of the liquid vessel. Alternative heating methods may be applied (rope heaters, cartridge heaters, or other types that will provide a controlled means of regulating liquid vessel temperature for the intended use duration). The temperature controlled within the system can be regulated between 35° C. and 70° C., for example, for the desired NO dose delivery to the patient.

a) A shuttle component can be cylindrical in shape with linear valves at each end. A shuttle can provide a number of design features:
   i. A cradle that can safely contain the glass ampoule and stabilize it during shipping and position the glass ampoule for breaking during system activation.
   ii. A shuttle can contain a pair of seals at each end to seal off their respective ports when required.
   iii. The seals at each end can be of different types. For example, Luer-like tapered seal coupled with a radial seal. These seals can be for redundancy and can interface their respective seats in the liquid module assembly.
   iv. A shuttle can incorporate a design feature whereby both end ports are closed as the glass ampoule is breaking. This can be accomplished by utilizing both radial seals on the shuttle.
   v. A shuttle can integrate a shield feature to shroud the patient flow port from glass shards entering after activation.
   vi. A shuttle can be fabricated from FEP, PTFE, PFA, for example, for contact chemical compatibility with $N_2O_4$. Alternatively, a metal shuttle with compliant seal(s) may be utilized. This may be stainless steel, titanium, aluminum, brass, and others, for example.
   vii. A shuttle can be connected to an activation rod, which can include a spring loaded such that the shuttle is forced to patient flow port closed/inerting chamber port open position. This can be for added safety.
   viii. The shuttle/liquid vessel clearances can be minimized to reduce volume within2 the liquid vessel.
b) The liquid vessel component can be cylindrical in shape with linear valve seats at each end. The liquid vessel can include a number of design features:
   i. Preferably constructed of metal (titanium, stainless steel, aluminum, other), the liquid vessel can house and contain the $N_2O_4$ and resultant $NO_2$ gas.
   ii. A liquid vessel can contain an interference feature along its inside wall that results in breaking the liquid ampoule as it passes. (Note: this interference feature can be a relative feature that could have also been included within or on the shuttle.)
   iii. A liquid vessel can contain a valve seat that interfaces the shuttle seals to the inerting chamber.
   iv. The exterior surface of a liquid vessel can be wrapped with a flexible heater (controlled by the console).
   v. The exterior surface of the liquid vessel can be surrounded by the inerting material (soda lime) contained in a plastic (polycarbonate, HDPE, ABS, etc.) material, again for safety. Alternatively, this chamber may be metal should there be concerns for a "take home" version be considered e.g., could the "dog eat it"). The inerting chamber may be placed anywhere contiguous with the liquid vessel discharge port.
   vi. A liquid vessel can contain a slow leak valve for $NO_2$ discharge into the inerting material. Alternatively, a slow leak valve may be positioned on the shuttle.

vii. A liquid vessel, if a separate component, can be affixed to the restrictor housing. A shuttle seat on the patient flow port may be contained in either component.
c) A slow leak valve can be a laser drilled element (ruby, stainless steel, titanium, etc.) component. A slow leak valve can provide a controlled release of $NO_2$ gas from the liquid vessel. The valve can be necessary during the discharge of $NO_2$ as the inerting chemical reaction forms a nitrate, and the reaction can be exothermic. Too rapid of a discharge could overheat the surrounding inerting material plastic surfaces. So as not to compromise the structural integrity of these surfaces, the $NO_2$ can be metered out so as to result in the discharge of the entire $N_2O_4$ converted contents within 10 minutes.
  i. A slow leak valve can have a controlled orifice of approximately 0.005 to 0.030".
  ii. The diameter to ID length are functionally related to control $NO_2$ discharge rate. Effectively, the larger the diameter of the orifice, the longer the lumen, so as to create a pressure drop to slow the $NO_2$ release.

Figure 22:
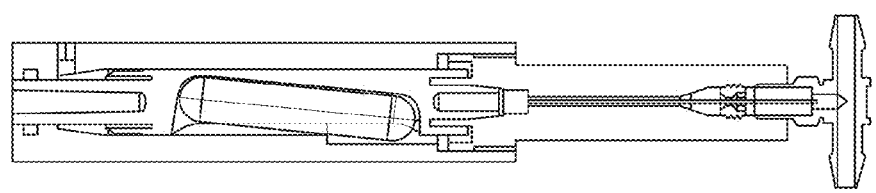
FIGS. 22-26 shows an exemplary shuttle mechanism in various configurations

Referring to FIG. 22, this depicts an exemplary shuttle mechanism. Initial position (shipping): inerting OPEN and patient flow CLOSED, glass ampoule intact. Neutralizer position is to the left and the patient position with the glass restrictor is to the right.

Figure 23:
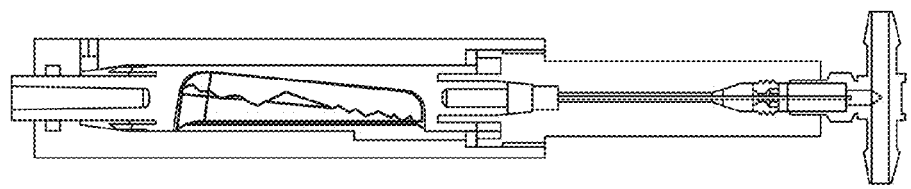

Referring to FIG. 23, this depicts the shuttle mechanism with both valves closed—the glass ampoule has been broken and the brown liquid $N_2O_4$ has spilled out of the glass.

Figure 24:
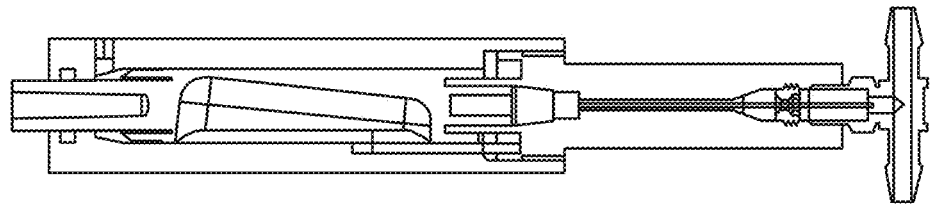

Referring to FIG. 24, this depicts the shuttle mechanism with Patient Flow Seal OPEN (right) & Inerting Seal (left) CLOSED.

Figure 25:
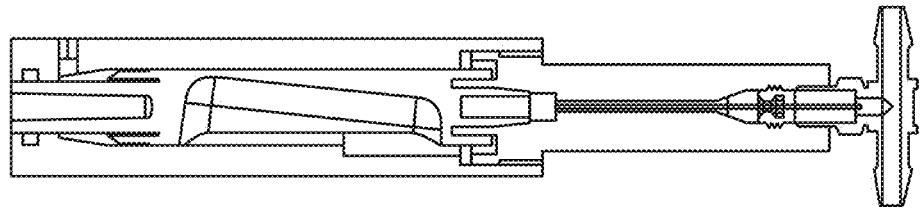

Referring to FIG. 25, this depicts the shuttle mechanism with the return position for cassette removal (same as initial shuttle position).

Figure 26:
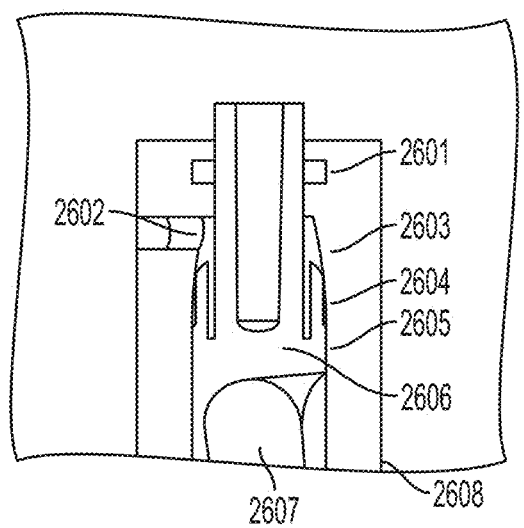

Referring to FIG. 26, a shuttle mechanism can include a liquid vessel/inerting chamber 2601, a slow leak valve 2602 (as an alternative design), an inerting seal seat 2603, shuttle inerting seals 2604 and Luer-like seal, a radial seal 2605, shuttle 2606, glass ampoule 2607 and $N_2O_4$, and a liquid vessel 2608.

Reaction Residence Time & Temperature

A restrictor housing can be an assembly comprising: a controlled orifice lumen and length, a sintered filter, a ferule to connect the controlled orifice column to the restrictor housing, a tee connector and attaching means to hermetically join the restrictor housing to the liquid vessel.

The restrictor housing can provide an assembly structure used to control delivery of $NO_2$ gas into an air steam (provided from the console). The $NO_2$ gas can mix with the air on its path to the conversion cartridge(s).

Heat can be applied to the restrictor housing (controlled by the console) to maintain a gas temperature 5° C. to 20° C. above the liquid vessel temperature to inhibit condensation from forming and plugging the controlled orifice column.

Figure 27:
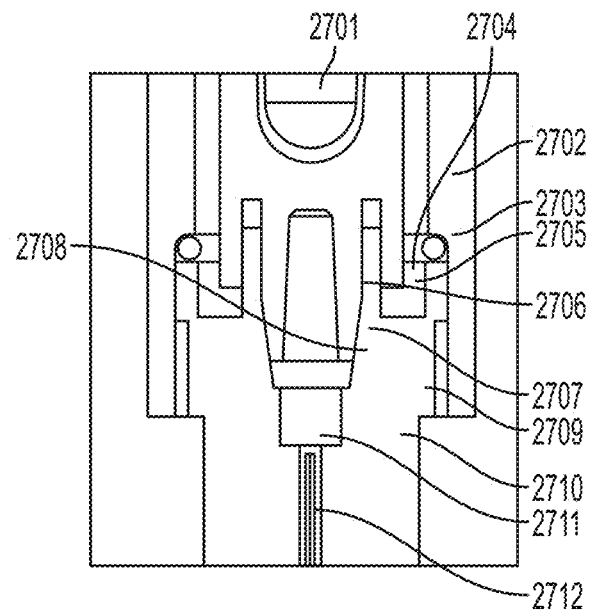
FIG. 27 shows an exemplary patient flow port liquid vessel/restrictor housing assembly.

The restrictor housing can include a number of components:
a) A restrictor column can be a static flow regulator that discharges $NO_2$ gas conditional upon the inlet pressure created in the liquid vessel. The pressure drop across the restrictor column can be a function of lumen diameter and lumen length.
  i. A restrictor column can manage a lumen diameter from 0.010 μm to 0.030 μm and a length from 1 cm to 4 cm.
  ii. A glass column can be extruded coated with a PTFE outer sleeve to protect the glass from handling damage and assembly compliance.
  iii. A restrictor column can be constructed of Type 1 Glass (preferred), but other restrictor materials may be utilized such as stainless steel, ruby, etc.
  iv. A restrictor column can be affixed to the restrictor housing utilizing a compressible ferule made from FEP, PTFE or PFA, for example.
  v. The column can be or include a fine bore quartz GC tubing that has been coated with Teflon instead of polyimide. Alternatively, a tiny orifice could be used that has the same pressure drop as the GC column. The advantage of using the relatively long column can be that the bore size can be large enough to minimize clogging Referring to FIG. 27, an exemplary patient flow port liquid vessel/restrictor housing assembly is shown. Such an assembly can include a glass ampoule 2701, a liquid vessel 2702, a Teflon crush washer 2703, a glass shroud 2704, a liquid vessel fluid reservoir 2705, shuttle patient flow seals such as a radial seal 2706, and a Luer like seal 2707, a patient flow seal seat 2708, a liquid vessel/restrictor housing joining means 2709, restrictor housing 2710, sintered filter 2711, and restrictor column 2712.
b) A restrictor housing can be a component, preferably metal, with the following features:
  i. A restrictor housing contains a lumen for assembling the restrictor column and securing ferule.
  ii. An alternative restrictor housing can incorporate a metal tube structure about the restrictor column which can be placed within the restrictor housing.
  iii. A restrictor housing can contain a flexible heater positioned on the outer cylindrical surface concentrated near the gas discharge end to maintain the A temperature between the liquid vessel and the restrictor column discharge.
  iv. A restrictor housing can be fabricated from metal. Titanium, stainless steel or aluminum are preferred materials.

Figure 28:
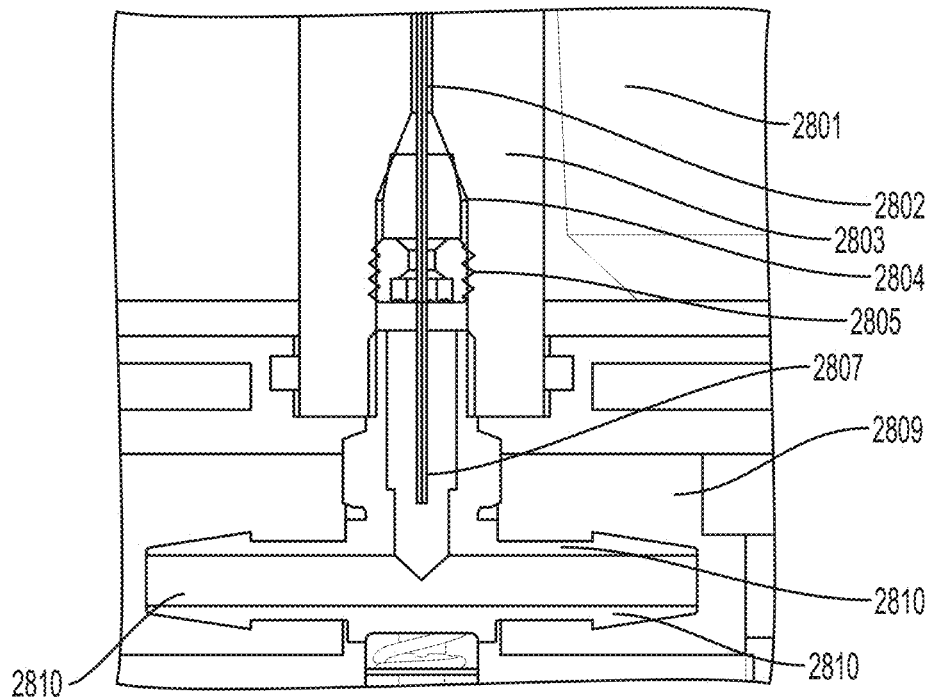
FIG. 28 shows a restrictor housing tee fitting assembly.

Referring to FIG. 28, a restrictor housing tee fitting assembly can include inerting material 2801, a restrictor column 2802, a restrictor housing 2803, a ferule 2804, a locking screw 2805, a $NO_2$ discharge 2806 from the restrictor column, base 2807, tee fitting 2808, air inlet 2809 and air/$NO_2$ outlet 2810.
c) A restrictor housing can contain a feature to affix a restrictor filter up-stream from the restrictor column;
  vi. A restrictor filter can be constructed of sintered titanium without a binder. It can also be made from stainless steel. It can also be coated with SiO2 to prevent reaction on its large surface area.
  vii. A restrictor filter can be press fitted into the restrictor housing or intermediate metal tube.

Other Liquid Module Components can be included in the assembly. These can include the inerting/purge chambers, inerting material, inerting chamber cap, purge/scrubber material, filler caps, and activation rod assembly.

Figure 29:
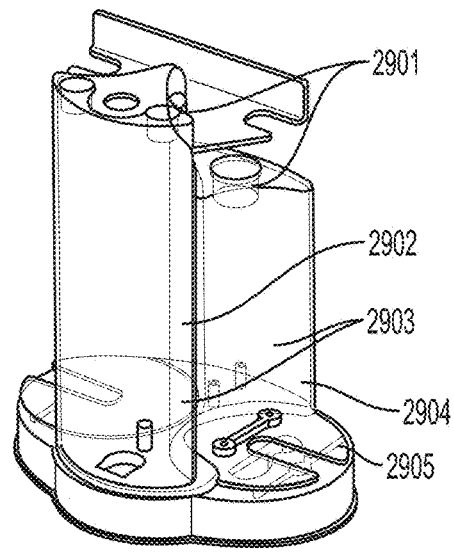
FIG. 29 shows a liquid module housing and base housing.

Referring to FIG. 29, a liquid module housing and base housing can include inerting material surrounding a liquid vessel/restrictor assembly and scrubbing material. Specifically, it can include chamber fill ports 2901, inerting chamber 2902 to be filled with soda lime, liquid module housing (chambers) 2903, scrubbing (purge) chamber 2904 to be filled with permanganate and a cartridge stabilizer 2905.

Figure 30:
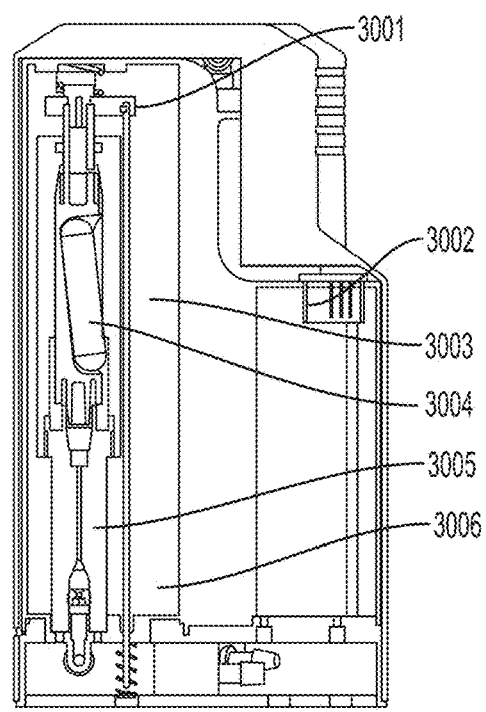
FIG. 30 shows a cassette cross-section through the inerting chamber and purge chamber.

Referring to FIG. 30, a cassette cross-section through the inerting chamber and purge chamber is depicted. This includes a shuttle/activation rod coupling 3001, a purge chamber 3002, an inerting chamber 3003, liquid vessel 3004, restrictor housing 3005, and shuttle activation rod 3006.

Figure 31:
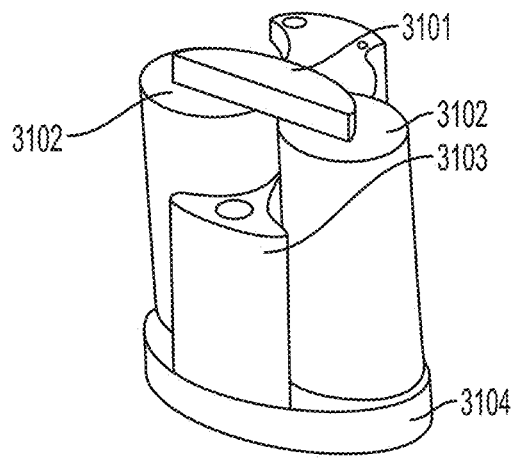
FIG. 31 depicts a cassette assembly.

Referring to FIG. 31, a cassette assembly is shown. This includes a cartridge bridge 3101, cartridges 3102, liquid module 3103 (with liquid vessel/restrictor assembly, inerting chamber and purge chamber), and base 3104.
- a) The inerting/purge chamber housing can be a polycarbonate structure to house the inerting material/liquid vessel/restrictor housing assembly and the purge/scrubbing material can be unique compartments. An inerting/purge chamber housing can have a number of design features:
  - i. An inerting chamber can completely house and encapsulate the liquid module assembly with the inerting material;
  - ii. An inerting chamber can provide a visual indication if the color change inerting material has changed color resulting from $NO_2$ exposure;
  - iii. An inerting chamber can contain an inerting chamber cap to which the restrictor housing can be connected and permit passage of the heater wires and temperature sensors (one with each heater). This cap can be sealed to result in a hermetically sealed chamber.
  - iv. A purge/scrubber chamber can provide an independent housing structure for the purge/scrubbing material used for console exhaust.
- b) An inerting material can be a blend of two materials. One material can provide effective $NO_2$ neutralization while the other material can exhibit a permanent color change when exposed to $NO_2$.
  - i. A primary inerting material can be soda lime (70-90% of mix).
  - ii. A permanent color change inerting material can be a different formulation of soda lime (balance of mix).
- c) A purge/scrubber material can be utilized to regulate the NO concentration delivered to the patient. In situations where the liquid module output may need to be reduced quickly (i.e., rapid temperature decrease), excess NO may be diverted to the Scrubber Material to neutralize it prior to environmental discharge. The material can oxidize NO to form $NO_2$. The substrate can absorb the $NO_2$.
  - i. A purge/scrubber material can be potassium permanganate on a substrate, such as a molecular sieve.
  - ii. An additional component of activated charcoal may be considered, or soda lime.
- d) The activation rod assembly can provide a spring loaded, normally closed patient flow port seal and can drive the shuttle one direction to break the glass ampoule and close the inerting chamber seal/open the patient flow port seal.
  - i. An activation rod assembly can be actuated by a feature within the console and can be tied to the lever activation handle.
  - ii. An activation rod can be coupled to the shuttle.

Conversion Cartridges $NO_2$ gas can be carried with room air that can be pumped into the liquid module tee (or "T") fitting at a flow rate of up to one liter per minute. The $NO_2$/Air mixture flows to the inlet of a first primary cartridge.

Figure 32:
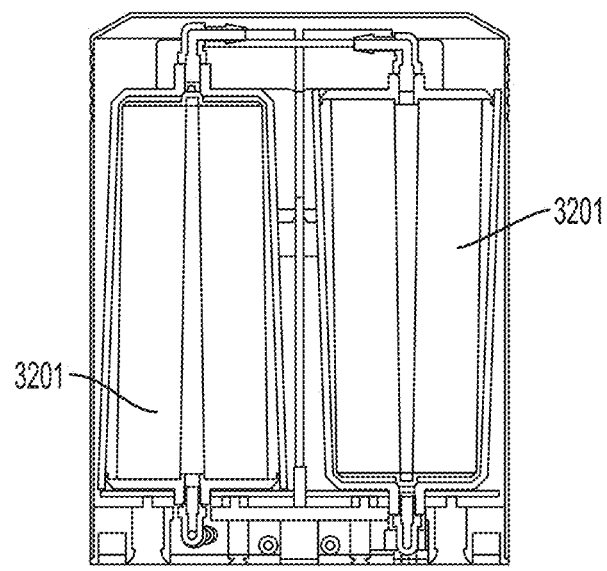
FIG. 32 shows a cross-section of a cassette through cartridges.

Referring to FIG. 32, a cross-section of a cassette through cartridges 3201 is depicted. With the cartridges in the cassette, gas flow is outside to inside.

A primary cartridge can contain a reducing agent included with a matrix, for example, ascorbic acid on silica gel which can react with $NO_2$ to form NO gas as the flow stream mixture crosses the cartridge wall.

A cartridge can include a number of components: a composite (which can be a matrix), a composite inlet cap, a composite outlet cap, a composite housing, a reducing agent (e.g., ascorbic acid coating), an inlet fitting with tubing and an outlet fitting with tubing.

Two cartridges can be placed in series post-restrictor column. Bridging from one subassembly to the next can utilize polyethylene tubing and barbed fittings, for example.

Figure 33:
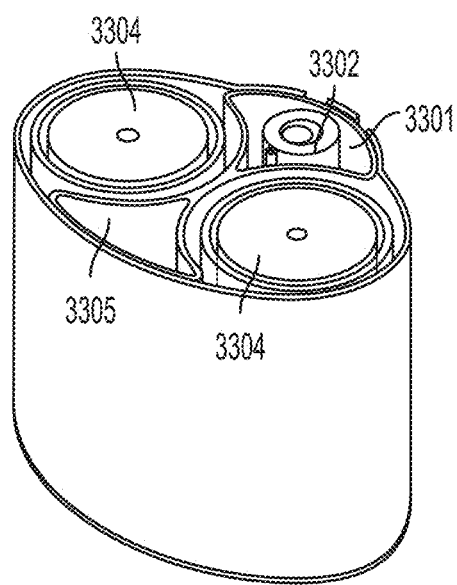
FIG. 33 shows a cross-section of a cassette.

Referring to FIG. 33, a cross-section of a cassette is shown. This depicts an inerting chamber 3301, liquid vessel with glass ampoule 3302, cartridges 3303, and a purge chamber 3304.
- a) A primary cartridge composite can be a matrix, for example, a blend of silica gel and HDPE.
  - i. A primary composite can be a blend of 45% to 85% silica gel to HDPE.
  - ii. A primary composite can be essentially cylindrical, having an outside surface and an inside surface where gas/air will flow from outside to inside (preferred) but also works well with flow from inside to outside.
  - iii. An HDPE can be utilized as a binder to produce a rigid composite structure. Alternatively, loosely packed silica gel may also be utilized
  - iv. The percent of a reducing agent (e.g., ascorbic acid) applied to a composite can be between 10% and 40%.
- b) A primary composite can be affixed to an inlet cap to direct gas/air flow through the side wall of a cartridge.
  - i. An inlet cap can be a HDPE component
  - ii. A design feature within an inlet cap can be a locating feature to pilot into the housing inlet port to provide stabilization for the cartridge during shipment, to effectively have both ends of the composite secured.
- c) A primary composite can be affixed to an outlet cap that flows NO gas from inside of the composite to discharge to the next subassembly.
  - i. An outlet cap can be a HDPE component
  - ii. An outlet cap can be affixed to the outer cartridge housing port to provide a hermetic enclosure for a cartridge.
- d) A primary cartridge housing can be the outer structure about the coated composite. These housings can provide physical protection to the composite during process storage, can provide a moisture barrier from the absorption of water during storage and can provide an oxygen barrier from permeation during storage.
  - i. A housing can be fabricated of HDPE.
  - ii. A composite can require a certain pressure (up to 5 psi) to drive the $NO_2$ or NO through the composite wall. A primary cartridge housing can retain that pressure permitting gas flow through the cartridge.
- e) The tubing and fittings can provide a conduit to advance the gas from one subassembly to another. Alternative methods and mechanisms for attaching components to other components are well known in the art and may include ultrasonic welding, spin welding, induction welding and other means.

The liquid module may be constructed in a radial configuration much like a petcock with two open positions (one for inerting and one for patient flow). This may be cylindrical or spherical shaped but dual seals can be used to prevent leakage between the ports.

The breaking of the glass ampoule can be currently a linear motion. A radial motion can also be utilized. This radial motion may contain a cam motion to radially and linearly occur simultaneously.

Other embodiments are within the scope of the following claims.

What is claimed is:

1. A cassette for conversion of nitrogen dioxide to nitric oxide comprising:
    a sealed housing,
    a first cartridge capable of converting nitrogen dioxide gas to nitric oxide within the sealed housing,
        the first cartridge comprising an inlet, a diverter, a body, an outlet, and a first porous solid matrix including a reducing agent,
        the first porous solid matrix being positioned within the first cartridge such that there is a space between the body of the first cartridge and the first porous solid matrix, wherein the first porous solid matrix includes an open passage parallel to the length of the body of the first cartridge,
    a second cartridge capable of converting nitrogen dioxide gas to nitric oxide, wherein an outlet of the first cartridge and an inlet of the second cartridge is connected,
        the second cartridge comprising an inlet, a diverter, a body, an outlet, and a second porous solid matrix including a reducing agent,
        the second porous solid matrix being positioned within the second cartridge such that there is a space between the body of the second cartridge and the second porous solid matrix wherein the second porous solid matrix includes an open passage parallel to the length of the body of the second cartridge; and
    an inerting chamber including a mixture including a nitrogen dioxide inerting material, wherein the inerting chamber connects the first cartridge and the second cartridge and is within the sealed housing.

2. The cassette of claim 1, wherein, in the first cartridge, the space has a width, which is a distance between the surface of the first porous solid matrix to the body of the first cartridge, and the width of the space is variable along the length of the receptacle, and wherein the inlet is configured to receive a gas flow, the diverter directs the gas flow to the space between the body and the first porous solid matrix, and the gas flow is fluidly communicated to the outlet through the first porous solid matrix to convert nitrogen dioxide in the gas flow into nitric oxide.

3. The cassette of claim 2, wherein the width of the space decreases along a portion of the length of the receptacle.

4. The cassette of claim 2, wherein the width of the space increases along a portion of the length of the receptacle.

5. The cassette of claim 4, wherein the width of the space increases along a portion of the length of the receptacle extending from the inlet to approximately the midpoint of the receptacle, and the width of the space decreases along a portion of the length of the receptacle extending from the approximately the midpoint of the receptacle to the outlet.

6. The cassette of claim 1, wherein the sealed housing further comprises a storage device of $N_2O_4$ and $NO_2$.

7. The cassette of claim 6, wherein the storage device is contained within a shuttle tube, wherein the tube stabilizes the storage device.

8. The cassette of claim 7, wherein the shuttle tube is positioned such that the inerting chamber opens to the storage device during shipment.

9. The cassette of claim 8, wherein the inerting material undergoes a permanent color change when the storage device is broken.

10. The cassette of claim 1, wherein the sealed housing further comprises a restrictor.

11. The cassette of claim 10, wherein the restrictor connects a storage device and the first cartridge.

12. The cassette of claim 1, wherein the sealed housing further comprises a heater.

13. The cassette of claim 12, wherein the heater wraps around a storage device and controls an output of nitrogen dioxide gas by changing the temperature of the storage device.

14. The cassette of claim 1, wherein the cassette is disposable after single use.

15. The cassette of claim 1, further connected to a console, wherein the console controls a heater.

16. The cassette of claim 1, wherein the inerting material removes $NO_2$.

* * * * *